(12) United States Patent
Kikuchi

(10) Patent No.: US 11,315,664 B2
(45) Date of Patent: Apr. 26, 2022

(54) MEDICAL INFORMATION PROCESSING APPARATUS, MEDICAL INFORMATION PROCESSING SYSTEM, MEDICAL INFORMATION PROCESSING METHOD, AND STORAGE MEDIUM

(71) Applicant: CANON KABUSHIKI KAISHA, Tokyo (JP)

(72) Inventor: Toru Kikuchi, Hino (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/685,193

(22) Filed: Aug. 24, 2017

(65) Prior Publication Data

US 2018/0060491 A1 Mar. 1, 2018

(30) Foreign Application Priority Data

Aug. 29, 2016 (JP) .............................. JP2016-167287

(51) Int. Cl.
*G16H 10/60* (2018.01)
*G16H 40/63* (2018.01)
(Continued)

(52) U.S. Cl.
CPC ......... *G16H 10/60* (2018.01); *G06F 21/6218* (2013.01); *G06T 7/0012* (2013.01); *G16H 15/00* (2018.01); *G16H 30/20* (2018.01); *G16H 40/63* (2018.01); *G06T 2207/30004* (2013.01); *H04L 63/08* (2013.01)

(58) Field of Classification Search
CPC ................................. G16H 30/00; G06F 19/00
See application file for complete search history.

(56) References Cited

U.S. PATENT DOCUMENTS

| 5,974,405 A | 10/1999 | McGuinness |
|---|---|---|
| 8,438,486 B2 | 5/2013 | Waldman |

(Continued)

FOREIGN PATENT DOCUMENTS

| JP | H08186762 A | 7/1996 |
|---|---|---|
| JP | 2003223509 A | 8/2003 |
| JP | 2013252345 A | 12/2013 |

OTHER PUBLICATIONS

Office Action issued in U.S. Appl. No. 15/710,896 dated Jul. 11, 2019.

(Continued)

*Primary Examiner* — Samantha (Yuehan) Wang
(74) *Attorney, Agent, or Firm* — Rossi, Kimms & McDowell LLP

(57) ABSTRACT

A medical information processing apparatus which processes structured information including a plurality of pieces of information obtained by classifying information about an imaging diagnosis and relation information indicating the relationships between the pieces of information includes an instruction unit configured to instruct pasting of the structured information, a decision unit configured to decide the layout direction of paste information in accordance with an instruction from the instruction unit, and a generating unit configured to generate paste data obtained by laying out the paste information in accordance with the layout direction, contents of the paste information, and the relation information.

25 Claims, 30 Drawing Sheets

(51) Int. Cl.
*G16H 15/00* (2018.01)
*G16H 30/20* (2018.01)
*G06F 21/62* (2013.01)
*G06T 7/00* (2017.01)
*H04L 29/06* (2006.01)

(56) References Cited

U.S. PATENT DOCUMENTS

| | | | |
|---|---|---|---|
| 9,075,899 B1* | 7/2015 | Reicher | ............... G16H 40/63 |
| 2003/0063134 A1* | 4/2003 | Lord | ............... H04L 29/06 |
| | | | 715/853 |
| 2005/0091603 A1 | 4/2005 | Chen et al. | |
| 2006/0085435 A1* | 4/2006 | Fam | ............... G06F 16/9027 |
| 2006/0274928 A1 | 12/2006 | Collins et al. | |
| 2007/0025606 A1 | 2/2007 | Gholap et al. | |
| 2007/0237377 A1 | 10/2007 | Oosawa | |
| 2007/0266309 A1 | 11/2007 | Sellman | |
| 2011/0002515 A1 | 1/2011 | Futami et al. | |
| 2011/0199390 A1 | 8/2011 | Iizuka | |
| 2013/0151954 A1 | 6/2013 | Ierullo | |
| 2014/0172458 A1* | 6/2014 | Ueda | ............... G06F 19/321 |
| | | | 705/3 |
| 2015/0287389 A1* | 10/2015 | Mese | ............... G09G 5/10 |
| | | | 345/207 |
| 2016/0048956 A1 | 2/2016 | Bryan et al. | |
| 2016/0364122 A1* | 12/2016 | Shimomura | ............... G06F 17/248 |
| 2017/0039192 A1 | 2/2017 | Mustafi | |
| 2017/0337329 A1 | 11/2017 | Liu et al. | |
| 2018/0032679 A1 | 2/2018 | Dandala | |
| 2018/0089371 A1* | 3/2018 | Matsuki | ............... G16H 30/20 |

OTHER PUBLICATIONS

Ono. "Decide type of data by "select format and paste."", Touch PC, Japan, Mainichi Communications Inc., Mar. 24, 1999. vol. 4, No. 4. pp. 51, 56, 57. Cited in NPL 2.
Office Action issued in Japanese Appln. No. 2016-167287 dated Jan. 24, 2020.
Office Action issued in U.S. Appl. No. 15/710,896 dated Dec. 31, 2019.
Office Action issued in U.S. Appl. No. 15/710,896 dated May 1, 2020.
Office Action issued in U.S. Appl. No. 15/710,896 dated Sep. 18, 2020.
Advisory Action issued in U.S. Appl. No. 15/710,896 dated Dec. 3, 2020.
Office Action issued in U.S. Appl. No. 15/710,896 dated Feb. 19, 2021.
Notice of Allowance issued in U.S. Appl. No. 15/710,896 dated Jun. 24, 2021.

* cited by examiner

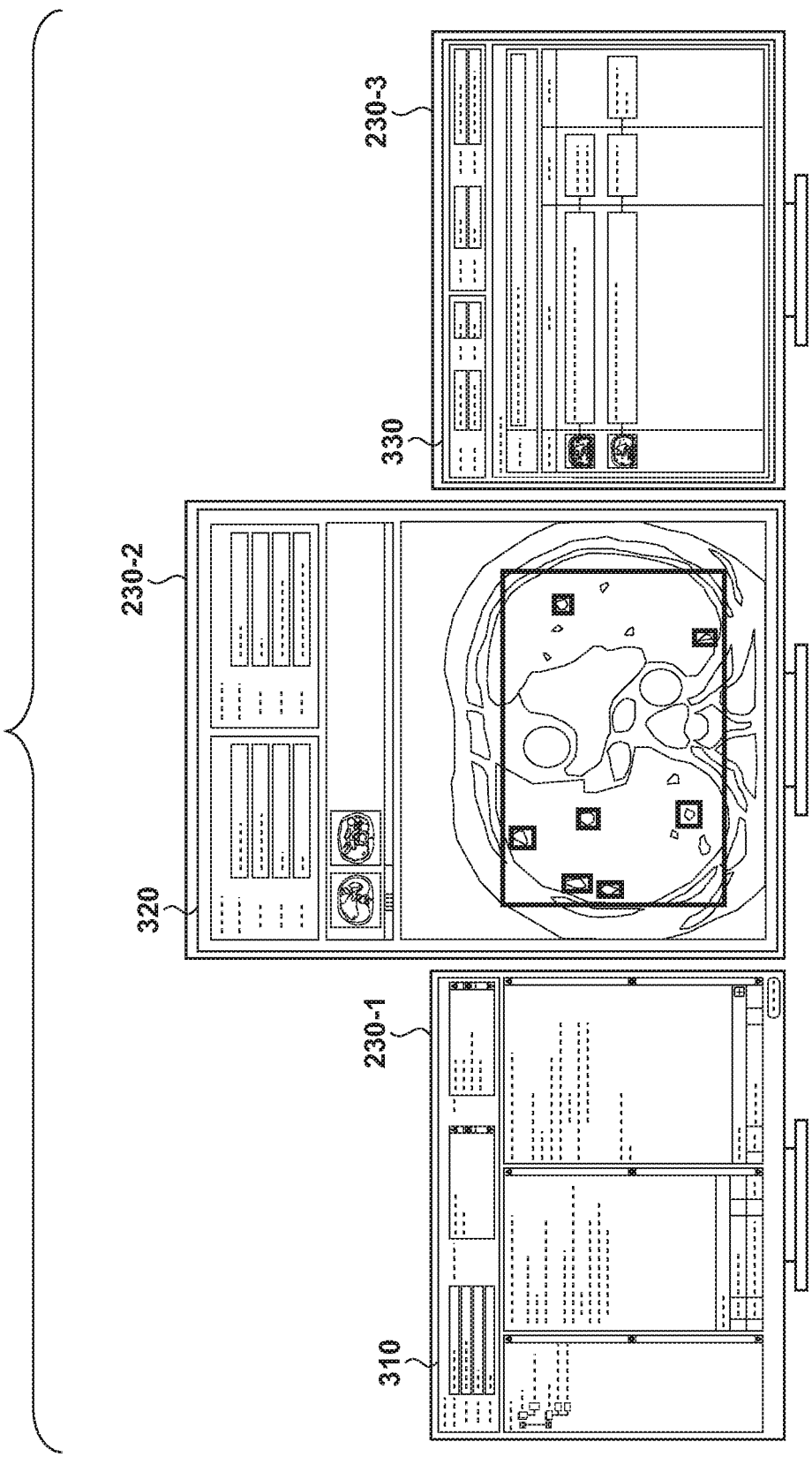

FIG. 3B

PATIENT INFORMATION — 311-1
- PATIENT NAME: SIMOMARUKO TARO
- PATIENT ID: P12335-26789
- AGE: 75 OLD
- SEX: MALE
- ALLERGY: BRONCHIAL ASTHMA / POLLEN ALLERGY — 313
- NOTE: [PAST MEDICAL HISTORY] 1996: PNEUMONIA; 2007: BRONCHIAL ASTHMA [FAMILY MEDICAL HISTORY] — 314

MEDICAL RECORD
- ☐ HEALTH RECORD
  - JULY 22, 2015
- ☐ EXAMINATION RESULT
  - JULY 22, 2015: PLAIN X-RAY EXAMINATION
  - AUGUST 23, 2015: CT

— 312

MAY 12, 2015 10:08: PAST HEALTH RECORD

[CHIEF COMPLAINT] LONG-LASTING COUGHING
[PRESENT CLINICAL HISTORY]
JULY 2015: HOSPITAL VISITING DUE TO LONG-LASTING COUGHING

S: LONG-LASTING COUGHING AND FATIGUE
O: CHEST PLAIN X-RAY SHOWED ABNORMAL SHADOW IN UPPER LUNG FIELD
A: DIFFUSE PANBRONCHIOLITIS IS SUSPECTED
P: ADMINISTRATION OF SMALL AMOUNT OF MACROLIDE ANTIBIOTIC
FOLLOW-UP BY THORACO-ABDOMINAL CT

TREATMENT/PRESCRIPTION

| | | | | |
|---|---|---|---|---|
| 1 | IMAGE | CHEST PLAN X-RAY | 1 | |
| 2 | ORAL ADMINISTRATION | xxxx TABLE (200 mg) ONE TABLET ONCE | 30 | DAYS |

PRESENT HEALTH RECORD: AUGUST 23, 2015 9:12

[MAIN COMPLAINT] LONG-LASTING COUGHING
[PRESENT CLINICAL HISTORY]
JULY 2015: HOSPITAL VISITING DUE TO LONG-LASTING COUGHING
JULY 2015: CHEST PLAIN X-RAY SHOWED ABNORMAL SHADOW IN UPPER LUNG FIELD
JULY 2015: DIFFUSE PANBRONCHIOLITIS IS SUSPECTED FOLLOW-UP BY CHEST PLAIN CT EXAMINATION

S: LONG-LASTING COUGHING AND FATIGUE
O:

TREATMENT/PRESCRIPTION

| | | | |
|---|---|---|---|
| 1 | IMAGE | CHEST PLAN CT | 1 |

— 310

CLOSE — 315

FIG. 3D

| PATIENT NAME | SIMOMARUKO TARO | AGE | 75 OLD |
|---|---|---|---|
| PATIENT ID | P12335-26789 | SEX | MALE |

| EXAMINATION TYPE | PLAIN CT | EXAMINATION DATE | AUGUST 23, 2015 11:23 |
|---|---|---|---|
| EXAMINATION REGION | CHEST REGION | COMMENT | HOSPITAL VISITING DUE TO LONG-LASTING COUGHING... |

AUGUST 23, 2015 11:23

REQUEST PURPOSE: CHEST PLAIN X-RAY SHOWED ABNORMAL SHADOW IN UPPER LUNG FIELD; DURING FOLLOW-UP

| REPRESENTATIVE IMAGE | FINDING | DIAGNOSIS | RECOMMENDATION |
|---|---|---|---|
| (336-1) | MULTIPLE NODULAR SHADOWS ARE NOTED IN BOTH LUNG FIELDS. SIZES ARE ..... SHAPES ARE ..... (337-1) | DIFFUSE PANBRONCHIOLITIS IS SUSPECTED (338-1) | PLEASE FOLLOW UP (339) |
| (336-2) | NODE IS NOTED IN RIGHT LUNG S2. SIZE IS ..... SHAPE IS ..... (337-2) | LUNG CANCER IS SUSPECTED (338-2) | |

| | REPORT INFORMATION | | |
|---|---|---|---|
| INFORMATION 1 | INFORMATION TYPE | REPORT INFORMATION | |
| | REPORT ID | R12335-26789 | |
| | INTERPRETATION DOCTOR | OTA HANAKO | |
| | INTERPRETATION DATE AND TIME | AUGUST 23, 2015 11:30:28 | |
| INFORMATION 2 | INFORMATION TYPE | PATIENT INFORMATION | |
| | PATIENT NAME | SIMOMARUKO TARO | |
| | PATIENT ID | P12335-26789 | |
| | AGE | 75 OLD | |
| | SEX | MALE | |
| INFORMATION 3 | INFORMATION TYPE | EXAMINATION INFORMATION | |
| | EXAMINATION TYPE | PLAIN CT | |
| | EXAMINATION REGION | CHEST REGION | |
| | EXAMINATION DATE | AUGUST 23, 2015 11:23:45 | |
| | REQUEST PURPOSE | HOSPITAL VISITING DUE TO LONG-LASTING COUGHING | |
| INFORMATION 4 | INFORMATION TYPE | COMMENT | |
| | UID | 1.3.12.2.1107.5.1.4.4853.... | |
| | CONTENTS | CHEST PLAN X-RAY SHOWED ABNORMAL ... IN UPPER LUNG FIELD | |
| INFORMATION 5 | INFORMATION TYPE | REPRESENTATIVE IMAGE | |
| | UID | 1.3.12.2.1107.5.1.4.4854.... | |
| | URL | http://xxxx.xxxx.xxx/4854... | |
| | ROI UID | 1.3.12.2.1107.5.1.4.5854.... | |

| | REPORT INFORMATION (CONTINUED) | | |
|---|---|---|---|
| INFORMATION 6 | INFORMATION TYPE | FINDING | |
| | UID | 1.3.12.2.1107.5.1.4.1234.... | |
| | FREE TEXT | MULTIPLE NODULAR SHADOWS ARE NOTED IN BOTH LUNG FIELDS | |
| | REGION NAME | BOTH LUNG FIELDS | |
| | LESION TYPE | MULTIPLE NODES | |
| INFORMATION 7 | INFORMATION TYPE | DIAGNOSIS | |
| | UID | 1.3.12.2.1107.5.1.4.2345.... | |
| | FREE TEXT | DIFFUSE PANBRONCHIOLITIS IS SUSPECTED ... | |
| | DIAGNOSIS NAME | DIFFUSE PANBRONCHIOLITIS | |
| INFORMATION 9 | INFORMATION TYPE | ROI | |
| | UID | 1.3.12.2.1107.5.1.4.5854.... | |
| | COORDINATES | X=..., Y=... | |
| | ROI NUMBER | 1 | |
| ... | ... | ... | |
| RELATION INFORMATION 1 | RELATION TYPE | MATCH | |
| | RELATION SOURCE UID | 1.3.12.2.1107.5.1.4.4854.... | |
| | RELATION DESTINATION UID | 1.3.12.2.1107.5.1.4.1234.... | |
| RELATION INFORMATION 2 | RELATION TYPE | CAUSE/GROUND | |
| | RELATION SOURCE UID | 1.3.12.2.1107.5.1.4.1234.... | |
| | RELATION DESTINATION UID | 1.3.12.2.1107.5.1.4.2345.... | |
| ... | ... | ... | |

F I G. 5B

502

| | | HEALTH RECORD | | |
|---|---|---|---|---|
| PATIENT INFORMATION | PATIENT NAME | SIMOMARUKO TARO | | |
| | PATIENT ID | P12335-26789 | | |
| | AGE | 75 OLD | | |
| | SEX | MALE | | |
| | ALLERGY | BRONCHIAL ASTHMA POLLEN ALLERGY | | |
| | NOTE | [PAST MEDICAL HISTORY] 1996: PNEUMONIA 2007: BRONCHIAL ASTHMA ... | | |
| MEDICAL RECORD | HEALTH RECORD | JULY 22, 2015 | | |
| | EXAMINATION RESULT | JULY 22, 2015: PLAIN X-RAY AUGUST 23, 2015: CT | | |
| HEALTH RECORD CONTENTS 1 | UPDATE DATE AND TIME | AUGUST 23, 2015 9:12 | | |
| | TEXT | [MAIN COMPLAINT] LONG-LASTING COUGHING [PRESENT CLINICAL HISTORY] JULY 2015: HOSPITAL VISITING DUE TO LONG-LASTING COUGHING ... S: LONG-LASTING COUGHING AND FATIGUE ... | | |
| | TREATMENT/ PRESCRIPTION | 1 | IMAGE | CHEST PLANE X-RAY | 1 |
| | | 2 | ORAL ADMINISTRATION | XXX TABLE (200 mg) | 30 DAYS |
| | ... | ... | ... | ... |
| HEALTH RECORD CONTENTS 2 | ... | | | |
| ... | | | | |

| | | IMAGE INFORMATION |
|---|---|---|
| PATIENT INFORMATION | PATIENT NAME | SIMOMARUKO TARO |
| | PATIENT ID | P12335-26789 |
| | AGE | 75 OLD |
| | SEX | MALE |
| EXAMINATION INFORMATION | EXAMINATION UID | 1.3.12.2.1107.5.1.4.9854.... |
| | EXAMINATION TYPE | PLAIN CT |
| | EXAMINATION REGION | CHEST REGION |
| | EXAMINATION DATE | AUGUST 23, 2015 11:23 |
| | COMMENT | HOSPITAL VISITING DUE TO LONG-LASTING COUGHING... |
| SLICE IMAGE INFORMATION 1 | IMAGE UID | 1.3.12.2.1107.5.1.4.4854.... |
| | SERIES UID | 1.3.12.2.1107.5.1.4.8854.... |
| | EXAMINATION UID | 1.3.12.2.1107.5.1.4.9854.... |
| | URL | http://xxxx.xxxx.xxx/4854 |
| SLICE IMAGE INFORMATION 2 | IMAGE UID | 1.3.12.2.1107.5.1.4.4855.... |
| | SERIES UID | 1.3.12.2.1107.5.1.4.8854.... |
| | EXAMINATION UID | 1.3.12.2.1107.5.1.4.9854.... |
| | URL | http://xxxx.xxxx.xxx/4855 |
| ... | ... | ... |

FIG. 6

| PASTE SETTING INFORMATION | SETTING INFORMATION | | |
|---|---|---|---|
| | DATA FORMAT | JPEG IMAGE | SELECTION |
| | | TEXT | NON-SELECTION |
| | | HTML | NON-SELECTION |
| | LAYOUT DIRECTION | VERTICAL | SELECTION |
| | | HORIZONTAL | NON-SELECTION |
| | | VERTICAL AND HORIZONTAL | NON-SELECTION |

600-1

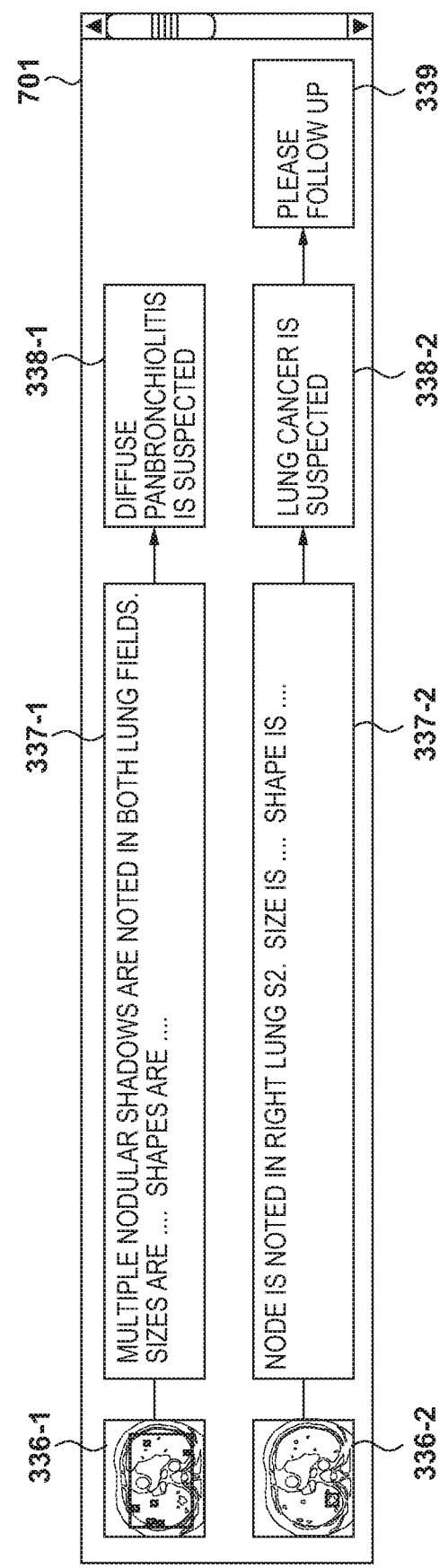

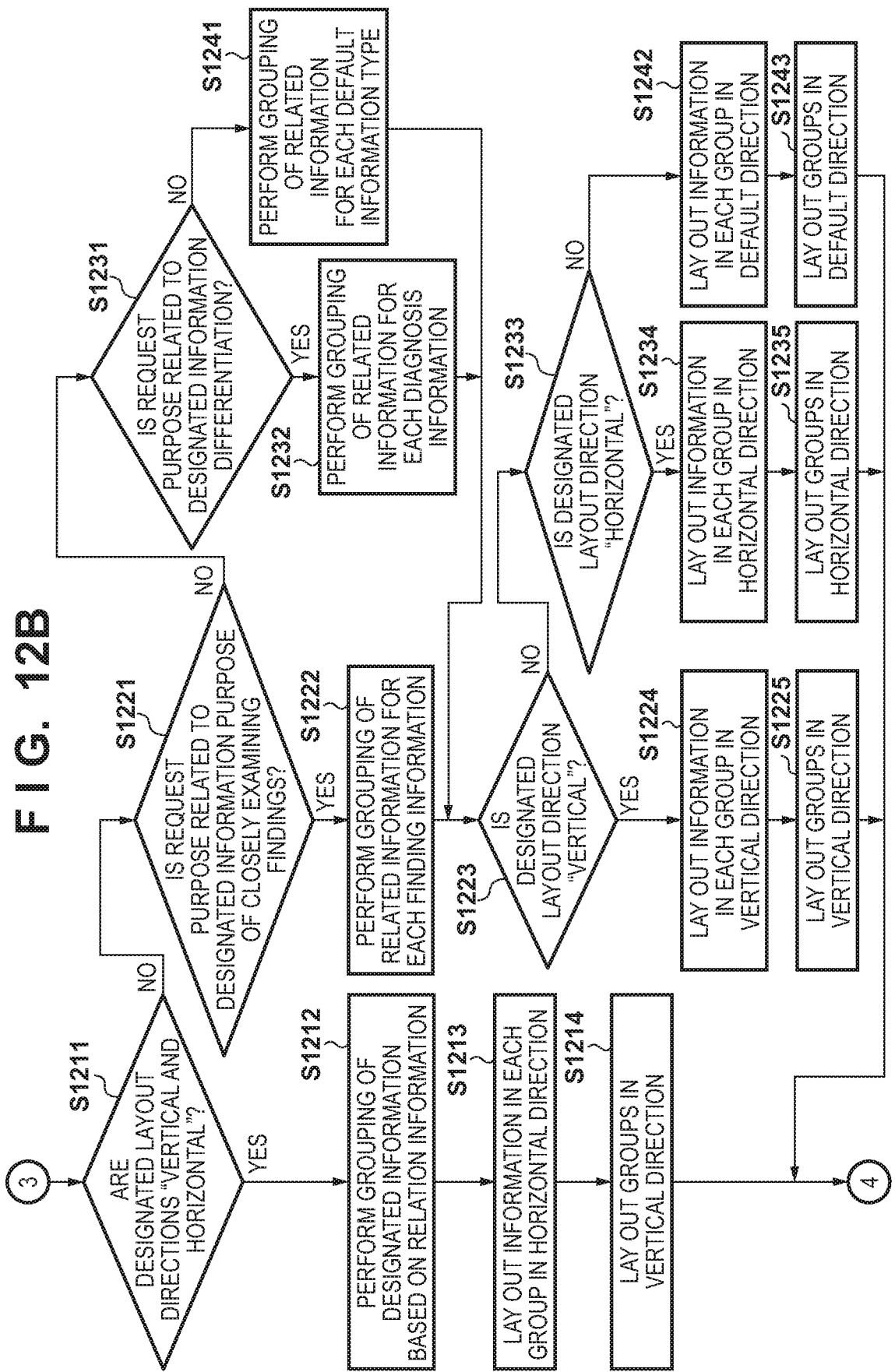

FIG. 15

| PASTE SETTING INFORMATION | | SETTING INFORMATION | |
|---|---|---|---|
| DATA FORMAT | JPEG IMAGE | SELECTION |
| | TEXT | NON-SELECTION |
| | HTML | NON-SELECTION |
| LAYOUT DIRECTION | VERTICAL | SELECTION |
| | HORIZONTAL | NON-SELECTION |
| | VERTICAL AND HORIZONTAL | NON-SELECTION |
| INFORMATION ADDITION | EXAMINATION INFORMATION | SELECTION |
| | REPORT URL | SELECTION |
| | IMAGE URL | SELECTION |
| | RELATION INFORMATION | SELECTION |

600-2

F I G. 18

PATIENT INFORMATION
| | |
|---|---|
| PATIENT NAME | SIMOMARUKO TARO |
| PATIENT ID | P12335-26789 |
| AGE | 75 OLD |
| SEX | MALE |

ALLERGY
BRONCHIAL ASTHMA
POLLEN ALLERGY

NOTE
[PAST MEDICAL HISTORY]
1996: PNEUMONIA
2007: BRONCHIAL ASTHMA
[FAMILY MEDICAL HISTORY]
...

MEDICAL RECORD
- HEALTH RECORD
  - JULY 22, 2015
- EXAMINATION RESULT
  - JULY 22, 2015: PLAIN X-RAY EXAMINATION
  - AUGUST 23, 2015: CT

MAY 12, 2015 10:08: PAST HEALTH RECORD

[CHIEF COMPLAINT] LONG-LASTING COUGHING
[PRESENT CLINICAL HISTORY]
JULY 2015: HOSPITAL VISITING DUE TO LONG-LASTING COUGHING

S: LONG-LASTING COUGHING AND FATIGUE
O: CHEST PLAIN X-RAY SHOWED ABNORMAL SHADOW IN UPPER LUNG FIELD
A: DIFFUSE PANBRONCHIOLITIS IS SUSPECTED
P: ADMINISTRATION OF SMALL AMOUNT OF MACROLIDE ANTIBIOTIC
FOLLOW-UP BY THORACO-ABDOMINAL CT

TREATMENT/PRESCRIPTION
| | IMAGE | CHEST PLAIN X-RAY | 1 | |
|---|---|---|---|---|
| 1 | | | | |
| 2 | ORAL ADMINISTRATION | xxxx TABLE (200 mg): ONE TABLET ONCE | 30 | DAYS |

PRESENT HEALTH RECORD: AUGUST 23, 2015 9:12

[MAIN COMPLAINT] LONG-LASTING COUGHING
[PRESENT CLINICAL HISTORY]
JULY 2015: HOSPITAL VISITING DUE TO LONG-LASTING COUGHING
JULY 2015: CHEST PLAIN X-RAY SHOWED ABNORMAL SHADOW IN UPPER LUNG FIELD
JULY 2015: DIFFUSE PANBRONCHIOLITIS IS SUSPECTED
FOLLOW-UP BY CHEST PLAIN CT EXAMINATION

S: LONG-LASTING COUGHING AND FATIGUE
O: [AUGUST 23, 2015: CHEST PLAIN CT EXAMINATION RESULT] — 1801
[IMAGE FINDING] MULTIPLE NODULAR SHADOWS ARE NOTED IN BOTH LUNG FIELDS
SIZES ARE .... SHAPES ARE ....
[IMAGING DIAGNOSIS] DIFFUSE PANBRONCHIOLITIS IS SUSPECTED — 1802

[REPORT URL:http://xxxx.xxx.xx/2345...] — 1803
[IMAGE URL:http://xxxx.xxx.xx/4854...]

TREATMENT/PRESCRIPTION
| | IMAGE | CHEST PLAN CT | 1 |
|---|---|---|---|
| 1 | | | |

310-2

CLOSE

MEDICAL INFORMATION PROCESSING APPARATUS, MEDICAL INFORMATION PROCESSING SYSTEM, MEDICAL INFORMATION PROCESSING METHOD, AND STORAGE MEDIUM

BACKGROUND OF THE INVENTION

Field of the Invention

The present invention relates to a medical information processing apparatus having a function of pasting the written contents of an interpretation report to other types of medical documents such as health records, a medical information processing system, a medical information processing method, and a storage medium.

Description of the Related Art

In recent years, with remarkable improvements in the performance of medical imaging apparatuses, it has been possible to obtain high-resolution three-dimensional image data (medical images) in a short time in CT (Computed Tomography), MRI (Magnetic Resonance Imaging), and the like. An interpretation doctor writes information obtained from medical images as a medical report. There is available an interpretation report introducing the idea of structuring for the purpose of allowing a person who reads the interpretation report to easily understand an increasing amount of information as described above. As a method of structuring interpretation reports, there is available a method of dividing the written content of a report into images, findings, diagnoses, recommendations, and the like and relating them.

One of structured interpretation reports has information arranged in accordance with relation information, with images, findings, diagnoses, and recommendations being arranged in the order named from the left in the lateral direction. Assume that the contents of such an interpretation report are pasted to a health record. In this case, if the width of each description field of the health record is not sufficient, the characters of the interpretation report decrease in size or the characters of one piece of information on one line decreases in number, resulting in illegibility. There is a need for a technique of changing the layout of information to be displayed on a window depending on the situation. There are the following two related arts.

Japanese Patent Laid-Open No. 2013-252345 discloses an ultrasonic imaging diagnosis apparatus which changes the window layout of ultrasonic images as display targets between vertical arrangement of the images and horizontal arrangement of the images in accordance with the luminance values of the shallow region and deep region of each image.

Japanese Patent Laid-Open No. 8-186762 discloses a mammography apparatus which performs control, based on settings, to lay out a specific one of right and left breast images, obtained in a specific imaging direction, in a specific one of right and left windows in a specific one of the vertical and horizontal directions in accordance with a doctor's preference or an abnormality detection result.

A structured interpretation report has pieces of information connected to each other via relation information to form a network structure. However, as disclosed in Japanese Patent Laid-Open Nos. 2013-252345 and 8-186762, simply changing the arrangement of pieces of information to be displayed to that in the vertical or horizontal direction can result in losing the relationships between the pieces of information expressed by relation information and lead to difficulty in understanding the content of the interpretation report.

The present invention provides a medical information processing technique of avoiding difficulty in understanding the contents of a structured interpretation report, when pasting the interpretation report to an electronic health record or the like, by laying out pasted data in accordance with the contents of the information of the interpretation report and relation information.

SUMMARY OF THE INVENTION

According to one aspect of the present invention, there is provided a medical information processing apparatus which processes structured information including a plurality of pieces of information obtained by classifying information about an imaging diagnosis and relation information indicating a relationship between the pieces of information, the apparatus comprising: an instruction unit configured to instruct pasting of the structured information; a decision unit configured to decide a layout direction of paste information in accordance with an instruction from the instruction unit; and a generating unit configured to generate paste data obtained by laying out the paste information in accordance with the layout direction, contents of the paste information, and the relation information.

According to the present invention, it is possible to perform a paste operation while avoiding difficulty in understanding the contents of a structured interpretation report, when pasting the report to a health record or the like, by laying out pasted data in accordance with the contents of information and relation information.

Further features of the present invention will become apparent from the following description of exemplary embodiments (with reference to the attached drawings).

BRIEF DESCRIPTION OF THE DRAWINGS

FIGS. 3A and 3B are views showing an example of the window arrangement of the medical information processing apparatus according to the first to third embodiments;

FIGS. 3C and 3D are views showing an example of the window arrangement of the medical information processing apparatus according to the first to third embodiments;

FIGS. 5A-5C are views showing an example of various types of information in the medical information processing apparatus according to the first to third embodiments;

FIG. 6 is a view showing an example of setting information in the medical information processing apparatus according to the first embodiment;

FIGS. 7A-7C are views showing an example of window display for explaining a layout direction in the medical information processing apparatus according to the first to third embodiments;

FIGS. 12A and 12B are flowcharts for pasted data generation processing in the medical information processing apparatus according to the first to third embodiments;

FIG. 15 is a view showing an example of setting information in the medical information processing apparatus according to the third embodiment;

FIG. 18 is a view showing an example of a health record window after the pasting of report information in the medical information processing apparatus according to the third embodiment.

DESCRIPTION OF THE EMBODIMENTS

Figure 1:
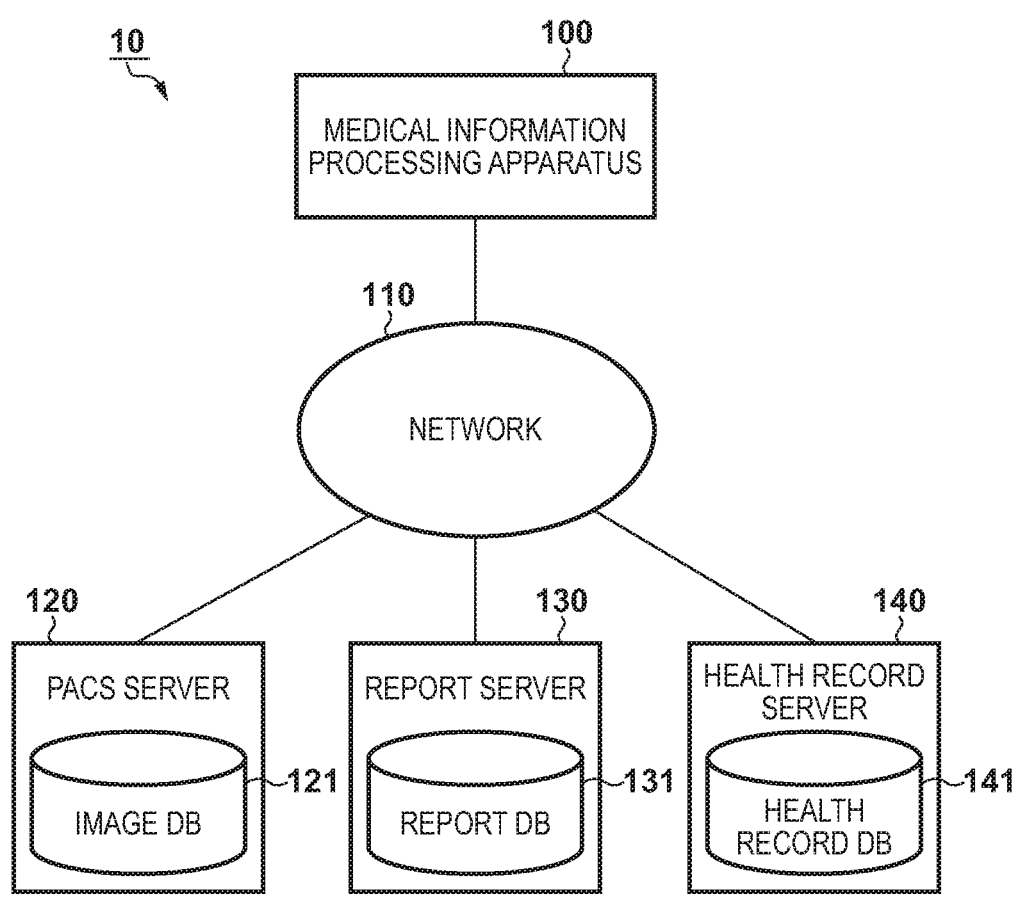
FIG. 1 is a block diagram showing the system configuration of a medical information processing system including a medical information processing apparatus according to the first to third embodiments.

Embodiments of the present invention will be exemplarily described in detail below with reference to the accompanying drawings. Note, however, that the constituent elements described in the embodiments are merely examples. The technical scope of the present invention is determined by the scope of claims and is not limited by the following individual embodiments. The same reference numerals denote the same items as those described in other embodiments unless otherwise specified, and a description of them will be omitted.

First Embodiment (System Configuration)

FIG. 1 shows the system configuration of a medical information processing system 10 including a medical information processing apparatus according to this embodiment. Assume that in the embodiment, pasted information (copy source information) is the structured information of an interpretation report generated by an imaging diagnosis based on images (medical images) obtained by a medical imaging apparatus such as a CT or MRI apparatus. Although the following description will exemplify an electronic health record (to be referred to as a health record hereinafter) as a paste destination, the same applies to a case in which other types of structured reports (structured medical reports) are pasted to other types of medical documents (medical document systems).

Referring to FIG. 1, the medical information processing system 10 includes a PACS (Picture Archiving and Communication System) server 120, a report server 130, a health record server 140, and a medical information processing apparatus 100. The PACS server 120 includes an image database (to be referred to as an image DB hereinafter) 121, and provides a function of storing and reading out image information via a network 110. Image information includes an image in a DICOM (Digital Imaging and Communications in Medicine) format obtained by a CT or MRI and information for managing the image. The detailed contents of such information will be described later with reference to FIG. 5C.

The report server 130 includes a report database (to be referred to as a report DB hereinafter) 131, and provides a function of storing and reading out report information via the network 110. The detailed contents of report information will be described later with reference to FIG. 5A. The health record server 140 includes a health record database (to be referred to as a health record DB hereinafter) 141, and provides a function of storing and reading out health record information via the network 110. The detailed contents of health record information will be described later with reference to FIG. 5B. The medical information processing apparatus 100 is an apparatus which cooperates with the PACS server 120, the report server 130, and the health record server 140 to browse an interpretation report and images concerning a patient as a diagnosis target so as to generate a health record.

(Hardware Arrangement)

Figure 2:
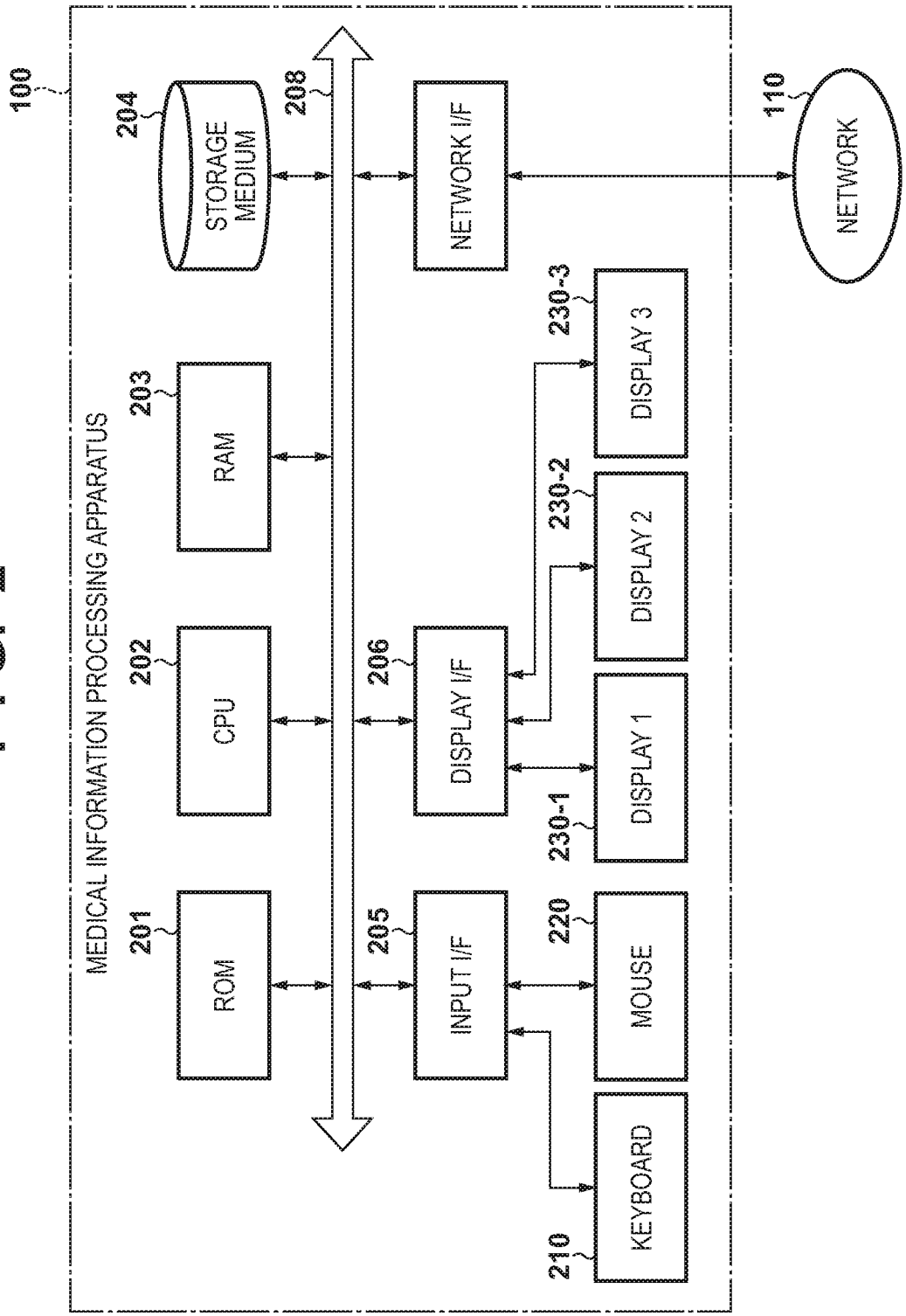
FIG. 2 is a block diagram showing the hardware arrangement of the medical information processing apparatus according to the first to third embodiments.

FIG. 2 shows the hardware arrangement of the medical information processing apparatus 100 according to this embodiment. Referring to FIG. 2, a storage medium 204 is, for example, an HDD (Hard Disk Drive) storing an OS (Operating System), processing programs, and various types of information. A ROM (Read Only Memory) 201 stores programs for starting up the OS, such as a BIOS (Basic Input Output System). A CPU (Central Processing Unit) 202 performs arithmetic processing when executing various types of programs. A RAM (Random Access Memory) 203 temporarily stores various types of information when the CPU 202 executes programs.

An input interface (to be referred to an I/F hereinafter) 205 is a communication interface such as a USB (Universal Serial Bus) for the connection of input devices such as a keyboard 210 and a mouse 220. A display I/F 206 is an interface such as a graphic board for the execution of window display on displays 230-1, 230-2, and 230-3. A network I/F 207 is an interface which complies with IEEE (Institute of Electrical and Electronics Engineers) 802.3ab or the like and is used to perform communication via the network 110. An internal bus 208 is used for communication by each block.

(Window Arrangement)

Figure 3C:
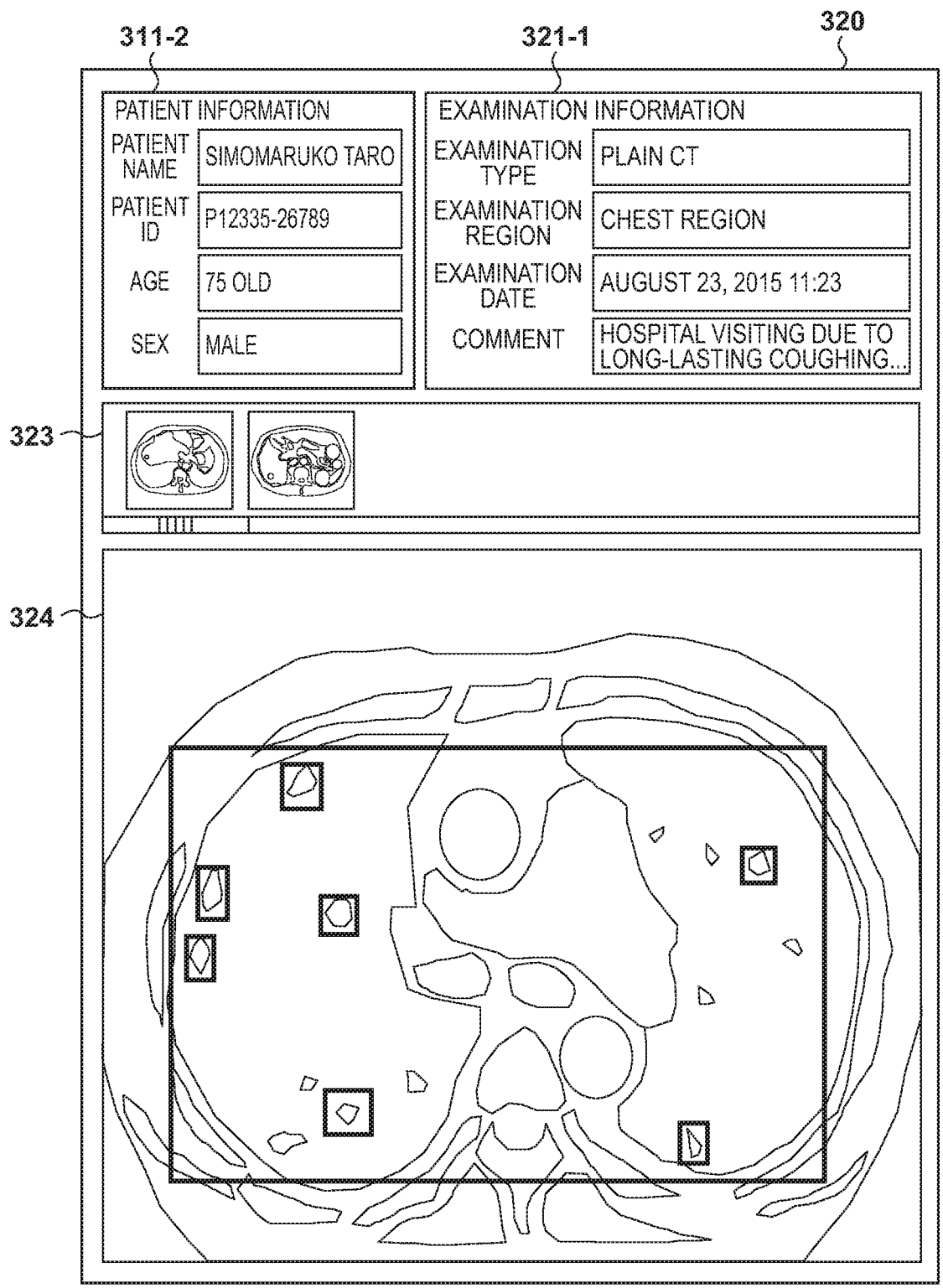

FIGS. 3A-3B and FIGS. 3C-3D are views each showing an example of the window arrangement of the medical information processing apparatus according to this embodiment. FIG. 3A shows the overall arrangement of the display windows of the medical information processing apparatus 100. A window 310 is a health record window for writing a medical record of a patient. A window 320 is a viewer window for browsing examination images such as CT and MRI images. A window 330 is a report window for browsing an interpretation report.

FIG. 3B is a view exemplarily showing the window arrangement of the health record window 310. The health record window 310 includes a patient information display area 311-1, a medical record display area 312, a past health record display area 313, a present health record editing area 314, and a button 315 for closing the health record window.

The patient information display area 311-1 displays information such as a patient name, patient ID, age, sex, allergy, and note. The medical record display area 312 displays a list of past health records and a list of examination results. When the user designates a past health record in the medical record display area 312, the past health record display area 313 displays the corresponding health record. When the user designates an examination result in the medical record display area 312, the window 330 and the window 320 display the corresponding examination report and images. The past health record display area 313 displays the date and time of creation of a health record, the text thereof, and details of a treatment/prescription. The present health record editing area 314 is configured to allow the user to edit/input a health record text and a treatment/prescription.

FIG. 3C shows the window arrangement of the viewer window 320. The viewer window 320 includes a patient information display area 311-2, an examination information display area 321-1, an examination image list display area 323, and an examination image display area 324. The patient information display area 311-2 displays information such as a patient name, patient ID, age, and sex. The examination information display area 321-1 displays information such as an examination type, examination region, examination date, and comment. The examination image list display area 323 displays a list of thumbnails of the images obtained by imaging in the same examination. The examination image display area 324 displays the image selected in the examination image list display area 323. This area allows the user to, for example, move a slice position to be displayed, change image display conditions such as WL (Window Level)/WW (Window Width), and graphically display an ROI (Region Of Interest) and the like.

FIG. 3D shows the window arrangement of the report window 330. The report window 330 includes a patient information display area 311-3, an examination information display area 321-2, a request purpose display area 333, and a report text display area 334. The patient information display area 311-3 displays information such as a patient name, patient ID, age, and sex. The examination information display area 321-2 displays information such as an examination type, examination region, examination date, and comment.

The request purpose display area 333 displays request information 335, which can be displayed upon being divided for each request purpose. An interpretation doctor may generate the request information 335 from information added to an interpretation request order or the like. Alternatively, the request side may generate the request information 335 when ordering an interpretation request.

The report text display area 334 displays an interpretation report in a structured document format including various types of information of an interpretation report which are obtained by classifying information about an imaging diagnosis according to predetermined types and relation information (links indicated by straight lines, arrows, and the like) for relating the respective types of information with each other. FIG. 3D exemplarily shows representative images, finding information, diagnosis information, and recommended information as examples of the respective types of information of the interpretation report. However, the scope of the present invention is not limited to these examples, and can include other types of information constituting the interpretation report.

The report text display area 334 displays representative images 336-1 and 336-2, pieces of finding information 337-1 and 337-2, pieces of diagnosis information 338-1 and 338-2, and recommended information 339. The interpretation doctor has input these pieces of information. The solid lines indicate the correspondence relationships between these pieces of information. The arrow lines indicate cause/ground relationships (cause-effect relationships). That is, in this embodiment, the finding information 337-1 corresponds to the representative image 336-1. The diagnosis information 338-1 corresponds to a diagnosis based on the finding information 337-1 as a cause/ground. Likewise, the finding information 337-2 corresponds to the representative image 336-2. The diagnosis information 338-2 corresponds to a diagnosis based on the finding information 337-2 as a cause/ground. The diagnosis information 338-2 and the recommended information 339 are related to each other. Note that the interpretation doctor inputs such relation information when generating a report. Referring to FIG. 3D, the solid lines indicate the correspondence relationships between the respective pieces of information, and the arrow lines indicate the cause/ground relationships. However, these indications are merely exemplary, and such relationships can be indicated by different types of lines.

(Functional Blocks)

Figure 4:
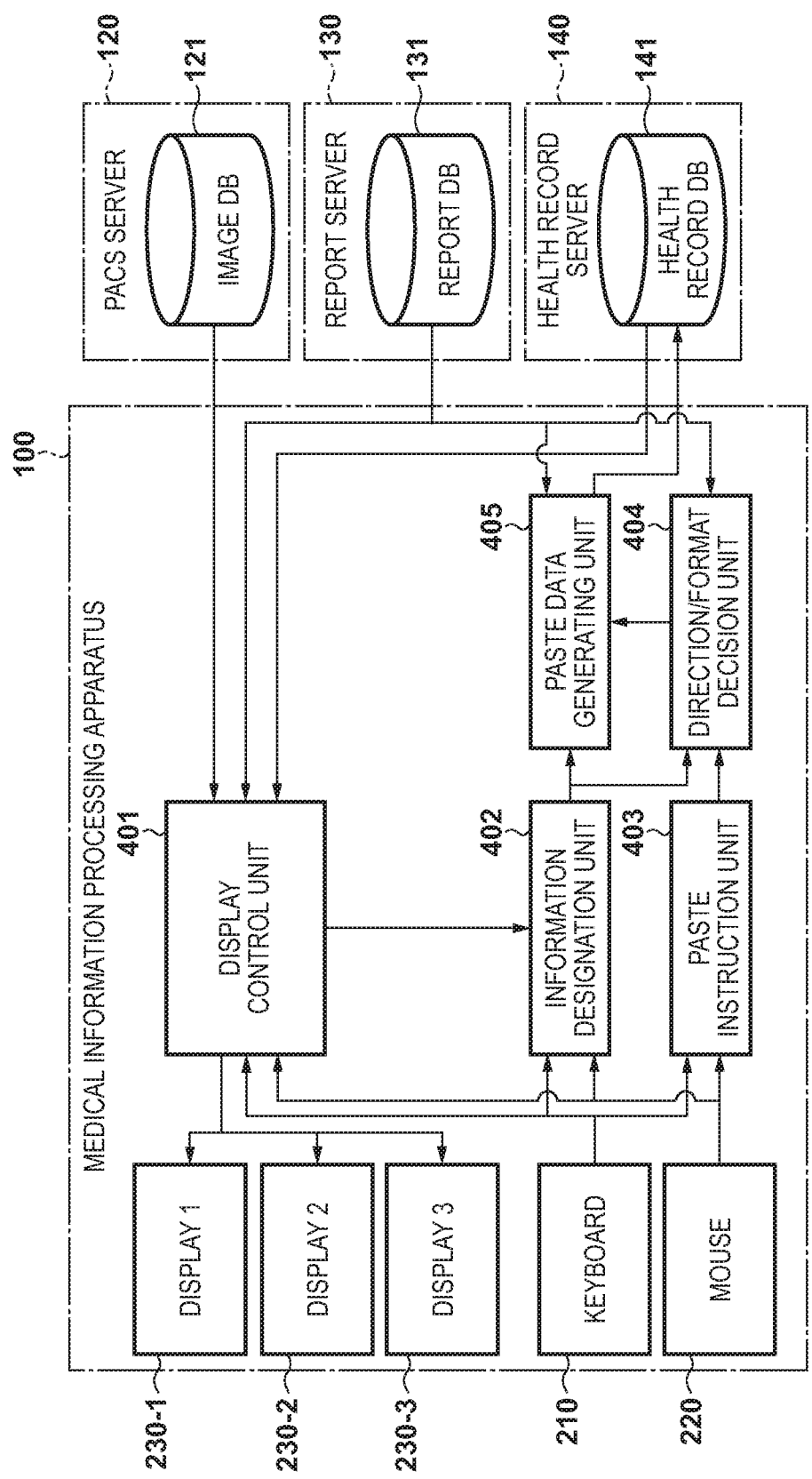
FIG. 4 is a functional block diagram of the medical information processing apparatus according to the first to third embodiments.

FIG. 4 is a functional block diagram of the medical information processing apparatus 100 according to this embodiment. The medical information processing apparatus 100 processes structured information (a structured interpretation report) including a plurality of pieces of information obtained by classifying information about an imaging diagnosis and relation information indicating the relationships between the pieces of information. The functional arrangement of the medical information processing apparatus 100 includes a display control unit 401, an information designation unit 402, a paste instruction unit 403, a direction/format decision unit 404 (decision unit), and a paste data generating unit 405.

The display control unit 401 reads out image information, report information, and health record information from the image DB 121, the report DB 131, and the health record DB 141, and controls the display of the viewer window 320, the report window 330, and the health record window 310 on display 1 (230-1) to display 3 (230-3). The display control unit 401 also updates the window display in the viewer window 320, the report window 330, and the health record window 310 in accordance with the operation of browsing image information, report information, and health record information. In addition, with regard to present health record information, the display control unit 401 edits and stores the health record information in the health record DB 141 upon reception of an editing input.

The information designation unit 402 provides a function of designating, as paste target information, all or part of the respective types of information constituting a structured interpretation report in the report window 330. The information designation unit 402 designates pieces of information constituting a structured interpretation report as paste target information. In this embodiment, the user can designate each piece of information such as request information, image information, finding information, diagnosis information, or recommended information by left-clicking on the corresponding portion with the mouse 220, and can also designate a plurality of pieces of information by left-clicking on the corresponding portion while pressing the Ctrl key on the keyboard 210.

The paste instruction unit 403 provides a function of issuing an instruction to paste the information designated by the information designation unit 402. Based on the designation made by the information designation unit 402, the paste instruction unit 403 issues an instruction to paste all or part of structured information (a structured medical report). In this embodiment, the user issues a paste instruction by pressing "Ctrl+C" on the keyboard 210 while information is designated, and then pressing "Ctrl+V" while the present health record editing area 314 as a paste destination is designated. Note that pressing "Ctrl+C" or "Ctrl+V" indicates simultaneously pressing the Ctrl key and the C key or the V key.

The direction/format decision unit 404 (decision unit) decides the data format and layout direction of data to be pasted based on the information designated by the information designation unit 402, report information, and the like in accordance with the paste instruction issued by the paste instruction unit 403. In this case, the layout direction is, for example, the vertical direction, the horizontal direction, or the vertical and horizontal directions. In addition, the data format is, for example, an image data format, a text data format, a structured data format (for example, XML (Extensible Markup Language), or an HTML (Hyper Text Markup Language) format.

The paste data generating unit 405 generates data to be pasted (paste data) by laying out information to be pasted in accordance with the data format and the layout direction decided by the direction/format decision unit 404, the information designated by the information designation unit 402, and relation information. The paste data generating unit 405 inputs the generated paste data in health record information and stores the resultant information in the health record DB 141 via the clip board function or the like provided by the OS.

The direction/format decision unit 404 (decision unit) and the paste data generating unit 405 perform the following processing. First of all, for example, the direction/format decision unit 404 decides the layout direction of paste information in accordance with the instruction issued by the paste instruction unit 403. The paste data generating unit 405 then generates paste data by laying out the paste information in accordance with the decided layout direction, the contents of the paste information, and relation information. The direction/format decision unit 404 then decides the data format of the paste information in addition to the layout direction. The paste data generating unit 405 can generate paste data in accordance with the data format decided by the direction/format decision unit 404. Note that the processing performed by the direction/format decision unit 404 (decision unit) and the paste data generating unit 405 is not limited to this example. For example, these units can also decide a data format and then lay out data after the decision of the data format.

(Various Types of Information)

FIGS. 5A-5C are views showing an example of various types of information in the medical information processing apparatus 100 according to this embodiment. FIG. 5A is a view showing an example of the arrangement of report information 501. The report information 501 includes a plurality of pieces of information obtained by classifying information about an imaging diagnosis and relation information indicating the relationships between the pieces of information. That is, the report information 501 includes a plurality of pieces of information (information 1, information 2, . . . ) constituting an interpretation report which is a report about an imaging diagnosis using a CT or MRI and a plurality of pieces of relation information (relation information 1, relation information 2, . . . ) indicating the relationships between the pieces of information.

Each piece of information has attribute information concerning an information type, and further includes attribute information defined in advance for each information type. Relation information has attribute information concerning a relation type and further has attribute information defined in advance. In this embodiment, the attribute types of information types include, for example, "report information", "patient information", "examination information", "request purpose", "representative image", "finding", "diagnosis", "recommendation", and "ROI". In addition, relation types include, for example, "match" and "cause/ground".

Report information has attribute information including a report ID, interpretation doctor, and imaging date. Patient information has attribute information including a patient name, patient ID, age, and sex.

In addition, examination information has attribute information including an examination type, examination region, examination date, and comment. A request purpose has attribute information including a UID (Unique Identifier) and contents (text). A representative image has a UID for uniquely identifying information, a URL (Uniform Resource Locator) for displaying an image in a viewer window, and an ROI UID for referring to information about a region of interest (ROI) added to the image.

A finding has attribute information including a UID, free text concerning the finding, region name, and lesion type. In this case, a region name and a lesion type may be extracted from a free text by language analysis, or the user may input them. A diagnosis has attribute information including a UID, free text, and diagnosis name. A recommendation has attribute information including a UID and a free text. An ROI has attribute information including a UID, coordinates, and ROI number. In addition, relation information has attribute information including relation source UID and a relation destination UID. Relation source and relation destination UIDs each correspond to one of the UIDs of a request purpose, representative image, finding, diagnosis, and recommendation.

FIG. 5B is a view showing an example of the arrangement of health record information 502. The health record information 502 includes patient information, medical record information, and a plurality of health record contents (health record contents 1, health record contents 2, . . . ) Patient information has attribute information including a patient name, patient ID, age, sex, allergy, and note. A medical record has attribute information including a health record and an examination result. Health record contents have attribute information including an update date and time, text, and treatment/prescription.

FIG. 5C is a view showing an example of the arrangement of image information 503. The image information 503 includes patient information, examination information, and a plurality of pieces of slice image information (slice image information 1, slice image information 2, . . . ) Patient information has attribute information including a patient name, patient ID, age, and sex. Examination information has attribute information including an examination UID, examination type, examination region, examination date, and comment. Slice image information has attribute information including an image UID, series UID, examination UID, and URL for displaying the image in the viewer window.

(Setting Information)

FIG. 6 is a view showing an example of setting information in the medical information processing apparatus according to this embodiment. Setting information 600-1 includes two pieces of information, namely a data format and a layout direction, as setting information (paste setting information) concerning pasting. The data format has information indicating "selection" or "non-selection" concerning, for example, a JPEG image, text, and HTML. The layout direction has information indicating "selection" or "non-selection" concerning, for example, each of directions, namely "vertical", "horizontal", and "vertical and horizontal". Note that a plurality of data formats and a plurality of layout directions may be set to "selection". When a plurality of such formats or directions are selected, the apparatus activates the operation of prompting the user to select one of them.

(Layout Direction)

Figure 7B:
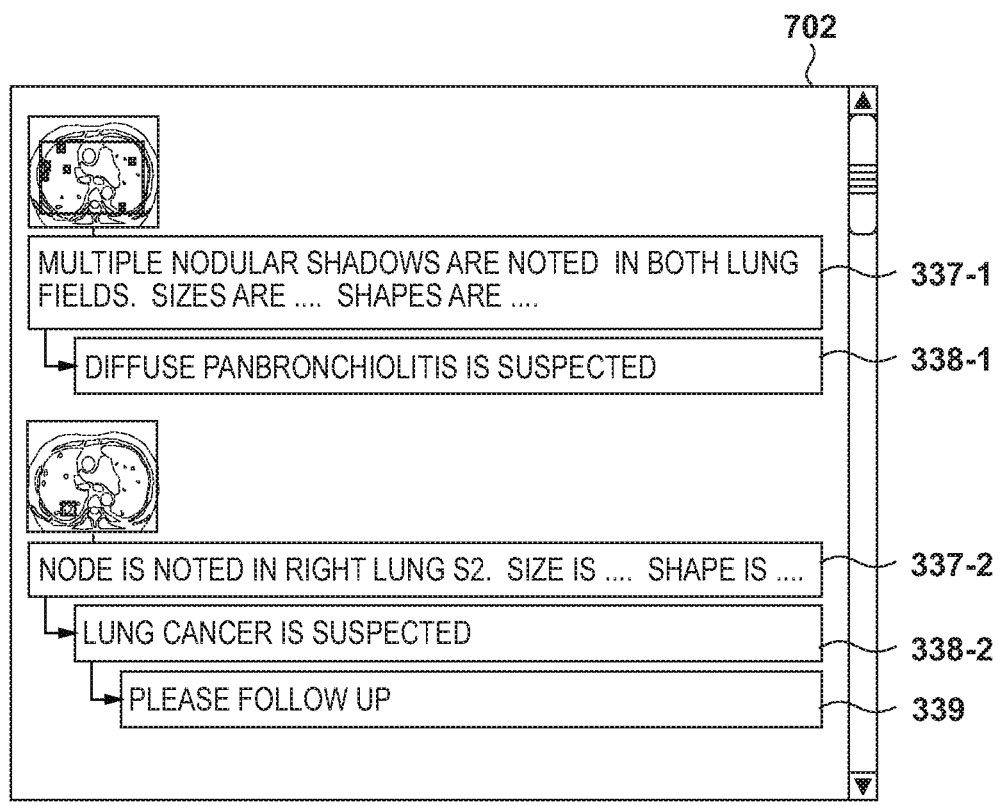
Figure 7C:
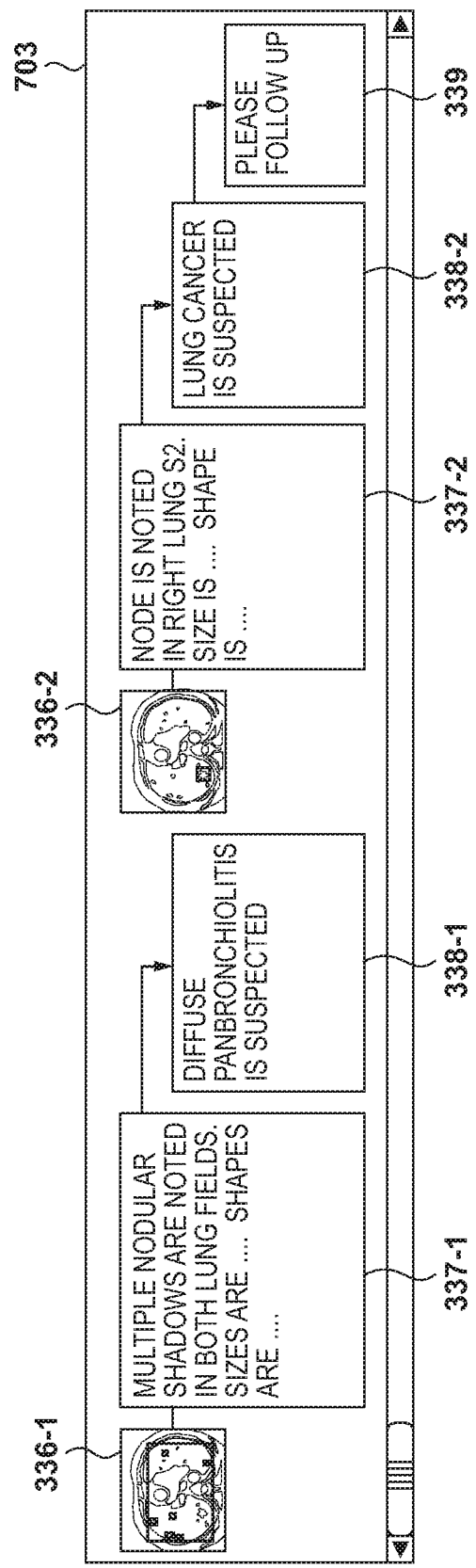

FIGS. 7A-7C are views each showing an example of window display for explaining a layout direction in the medical information processing apparatus according to this embodiment. FIG. 7A is a view showing an example of window display when the layout directions are "vertical and horizontal". When the layout directions are "vertical and horizontal", the representative image 336-1, the finding information 337-1, and the diagnosis information 338-1 belonging to a related information group are laid out in the horizontal direction in the group, and the respective groups are laid out in the vertical direction.

FIG. 7B is a view showing an example of window display when the layout direction is "vertical". When the layout direction is "vertical", the representative image 336-1, the finding information 337-1, and the diagnosis information 338-1 belonging to a related information group are laid out in the vertical direction in the group, and the respective groups are also laid out in the vertical direction.

FIG. 7C is a view showing an example of window display when the layout direction is "horizontal". When the layout direction is "horizontal", the representative image 336-1, the finding information 337-1, and the diagnosis information 338-1 belonging to a related information group are laid out in the horizontal direction in the group, and the respective groups are also laid out in the horizontal direction.

(Health Record Window after Report Information Pasting)

Figure 8:
FIG. 8 is a view showing an example of a health record window after the pasting of report information in the medical information processing apparatus according to the first and second embodiments.

FIG. 8 is a view showing an example of a health record window after report information pasting in the medical information processing apparatus according to this embodiment. A health record window 310-1 displays pasted report information 801. FIG. 8 shows an example of a window in which the representative image 336-1, the finding information 337-1, and the diagnosis information 338-1 are pasted when the layout direction is "vertical".

(Layout of Information)

Figure 9:
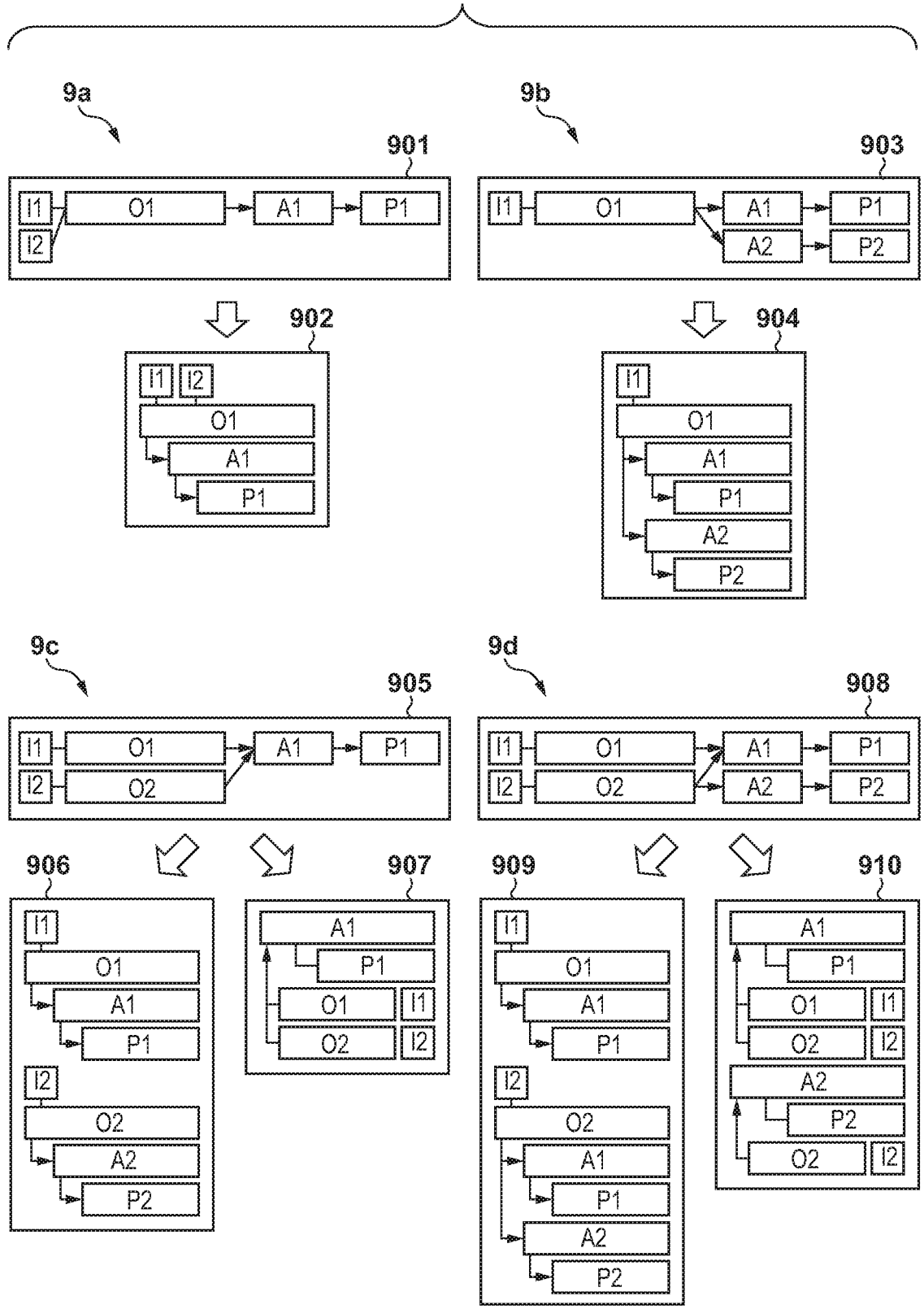
FIG. 9 is a view for explaining an example of a layout in the medical information processing apparatus according to the first to third embodiments.

9a to 9d in FIG. 9 are views each for explaining an example of a layout in the medical information processing apparatus according to this embodiment. 9a in FIG. 9 shows representative images I1 and I2, finding information O1, diagnosis information A1, and recommended information P1. Referring to 9a in FIG. 9, report information is laid out, with the two representative images I1 and I2, the one piece of finding information O1, the diagnosis information A1, and the recommended information P1 being related to each other. 9a in FIG. 9 shows an example 901 in which information is laid out in the vertical and horizontal directions, and an example 902 in which information is laid out in the vertical direction.

9b in FIG. 9 shows the representative image I1, the finding information O1, the diagnosis information A1 and diagnosis information A2, and the recommended information P1 and recommended information P2. Referring to 9b in FIG. 9, report information is laid out, with the one representative image I1, the one piece of finding information O1, the two pieces of diagnosis information A1 and A2, and the one piece of recommended information P1 or P2 being related to each other for each diagnosis information. 9b in FIG. 9 shows an example 903 in which information is laid out in the vertical and horizontal directions, and an example 904 in which information is laid out in the vertical direction.

9c in FIG. 9 shows the representative images I1 and I2, the finding information O1 and finding information O2, the diagnosis information A1, and the recommended information P1. Referring to 9c in FIG. 9, report information is laid out, with two sets ((I1, O1) and (I2, O2)), each having one representative image related to one piece of finding information, being related to the one piece of diagnosis information A1 and the one piece of recommended information P1. 9c in FIG. 9 shows an example 905 in which information is laid out in the vertical and horizontal directions, and an example 906 in which information is laid out in the vertical direction in each group for each finding, with the information being divided into information belonging to two groups, namely the group of the finding information O1 and the group of the finding information O2. In this case, the diagnosis information A1 and the recommended information P1 are related to both the pieces of finding information O1 and O2, and hence appear in the two groups. 9c in FIG. 9 also shows an example 907 in which information is laid out in the vertical direction in each group for each diagnosis, with the recommended information P1, the pieces of finding information O1 and O2, and the pieces of image information I1 and I2 being laid out in one group, namely the group of the diagnosis information A1.

9d in FIG. 9 shows the representative images I1 and I2, the pieces of finding information O1 and O2, the pieces of diagnosis information A1 and A2, and the pieces of recommended information P1 and P2. Referring to 9d in FIG. 9, report information is laid out, with two sets ((I1, O1) and (I2, O2)), each having one representative image related to one piece of finding information, being related to one piece of diagnosis information and one piece of recommended information, and one set (I2, O2) of the two sets being related to the other diagnosis information and the other recommended information. 9d in FIG. 9 shows an example 908 in which information is laid out in the vertical and horizontal directions, an example 909 in which information is laid out in the vertical direction in each group for each finding, with the information being divided into information belonging to two groups, namely the group of the finding information O1 and the group of the finding information O2, and an example 910 in which information is laid out in the vertical direction in each group for each diagnosis, with the information being divided into information belonging to two groups, namely the group of the diagnosis information A1 and the group of the diagnosis information A2. In this case, the finding information O2 and the image information I2 are related to both the pieces of diagnosis information A1 and A2, and hence appear in the two groups.

(Main Processing Procedure)

Figure 10A:
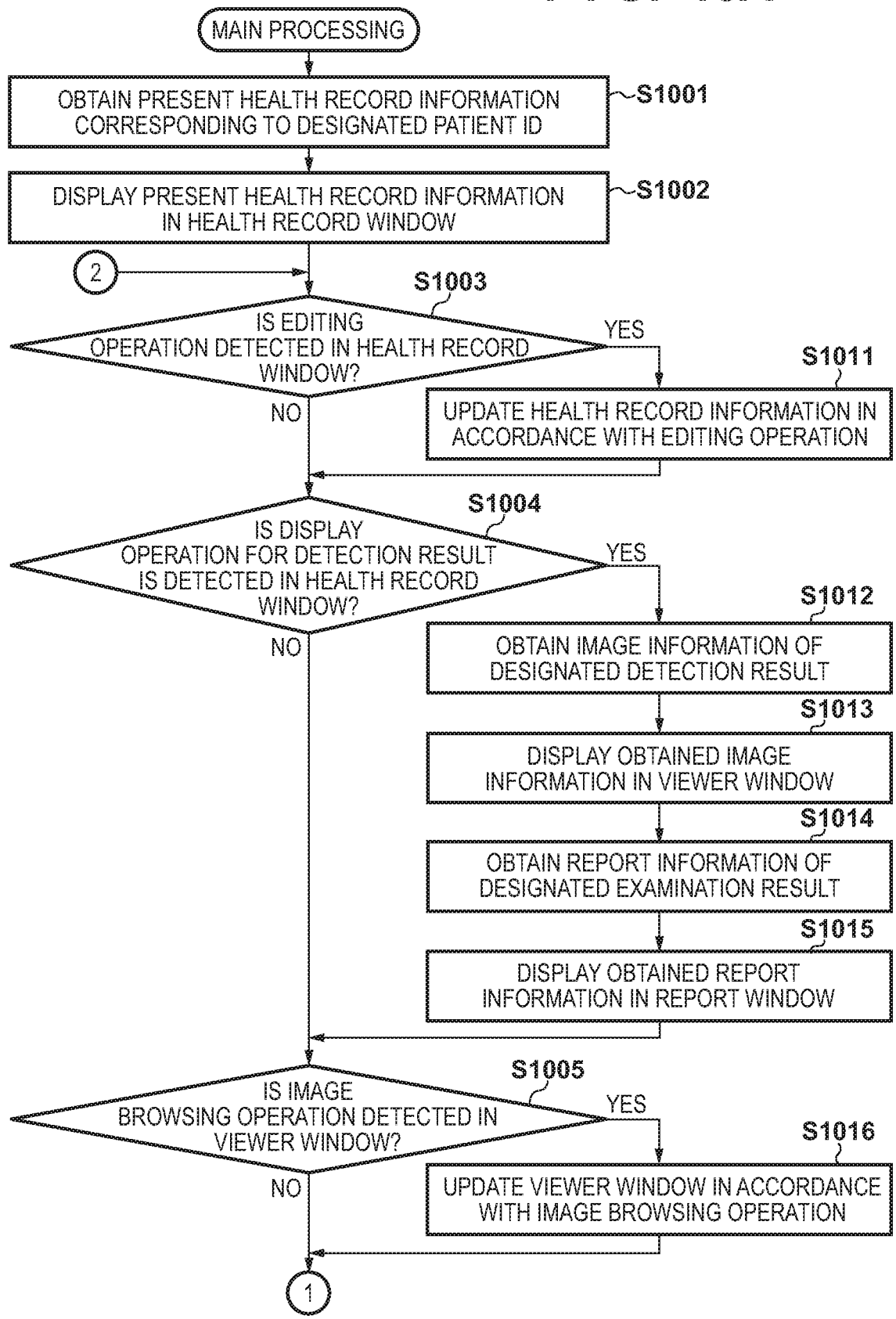
FIGS. 10A and 10B are flowcharts for main processing in the medical information processing apparatus according to the first embodiment.
Figure 10B:
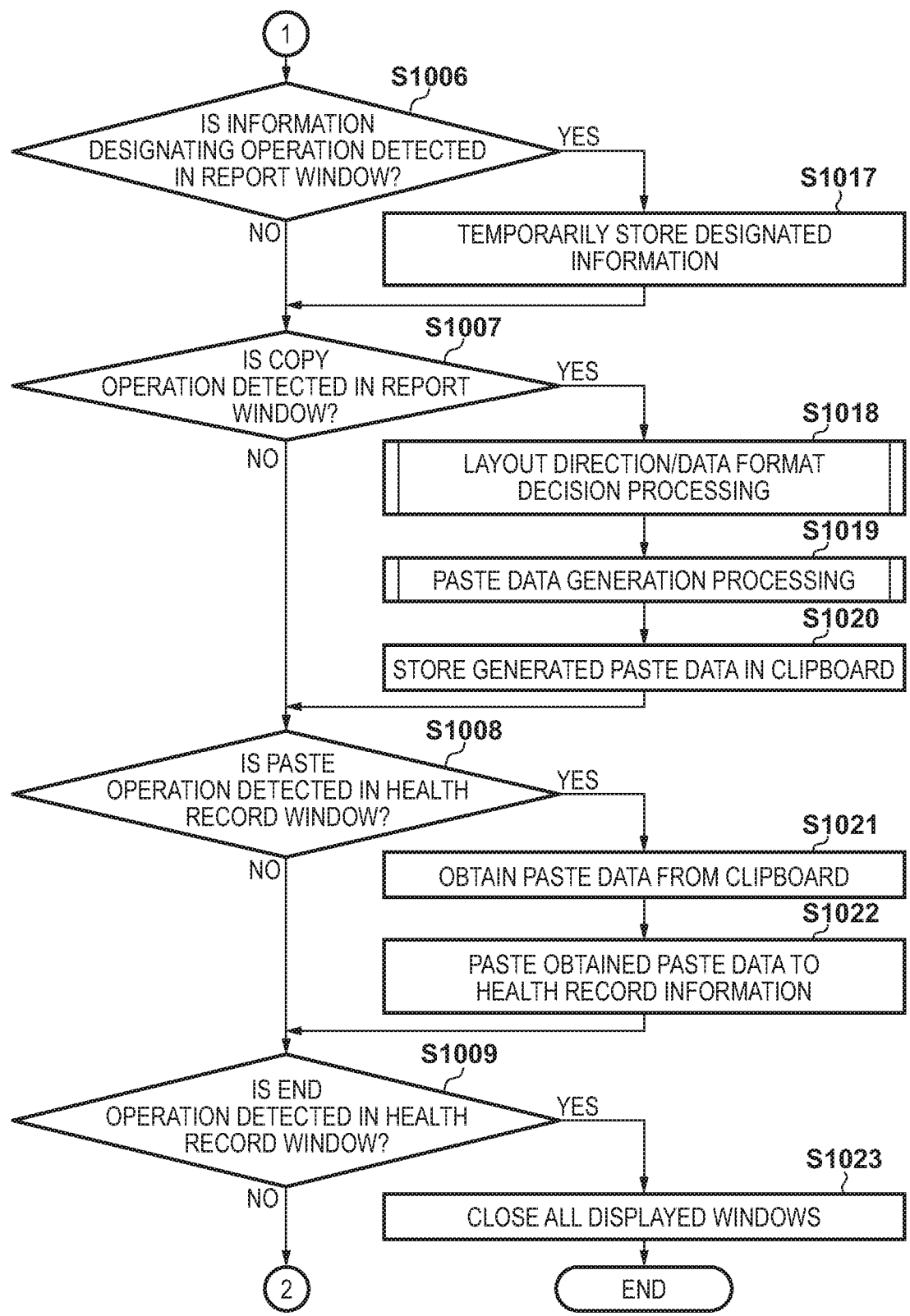

FIGS. 10A and 10B are flowcharts for main processing in the medical information processing apparatus according to this embodiment. When main processing starts, the display control unit 401 obtains the present health record information corresponding to the patient ID designated at the start of the processing from the health record DB 141 (step S1001), and displays the present health record information in the health record window 310 (step S1002).

In addition, upon detecting a health record editing operation in the health record window 310 (YES in step S1003), the display control unit 401 updates the health record information in accordance with the editing operation (step S1011). In this case, the health record editing operation includes inputting characters, deleting characters, and adding, deleting, and correcting treatment/prescription.

Upon detecting an examination result display operation in the health record window 310 (YES in step S1004), the display control unit 401 obtains the image information of the designated examination result from the image DB 121 (step S1012). Subsequently, the display control unit 401 displays the obtained image information in the viewer window 320 (step S1013). The display control unit 401 then obtains the report information of the designated examination result from the report DB 131 (step S1014), and displays the obtained report information in the report window 330 (step S1015). In this case, the examination result display operation includes left-double-clicking on the examination result in the medical record display area 312.

Upon detecting an image browsing operation in the viewer window 320 (YES in step S1005), the display control unit 401 updates the viewer window in accordance with the image browsing operation (step S1016). In this case, the image browsing operation includes moving the position of a slice to be displayed and changing an image display condition such as WL (Window Level)/WW (Window Width), and is assigned to dragging of the mouse in the vertical or horizontal direction or the like.

Upon detecting an information designating operation in the report window 330 (YES in step S1006), the information designation unit 402 temporarily stores the designated information (step S1017). In this case, the information designating operation includes clicking on information in the report window 330 with the mouse. Clicking while pressing the Ctrl key allows the user to select a plurality of pieces of information. In addition, simultaneous pressing the Ctrl key and the A key allows the user to select all the representative image, finding, diagnosis, and recommended information in the report.

If the paste instruction unit 403 detects a paste operation (copy operation) in the report window 330 (YES in step S1007), the direction/format decision unit 404 executes layout direction/data format decision processing (to be described with reference to FIG. 11) (step S1018). Subsequently, the paste data generating unit 405 executes paste data generation processing (to be described with reference to FIGS. 12A and 12B) (step S1019) and stores the generated paste data in a clipboard provided by the OS (step S1020).

If the paste instruction unit 403 detects a paste operation in the health record window 310 (YES in step S1008), paste data is obtained from the clipboard (step S1021), and the obtained paste data is pasted on the health record information (step S1022). Although this embodiment has exemplified the case in which a paste operation is divided into a copy operation and a paste operation, the same applies to a case in which a paste operation is one (one series) operation such as dragging and dropping. Upon detecting an end operation in the health record window 310 (YES in step S1009), the display control unit 401 closes all the displayed windows (step S1023), and terminates the processing. In this case, an end operation is, for example, clicking of the button 315 in the health record window 310.

(Layout Direction/Data Format Decision Processing Procedure)

Figure 11:
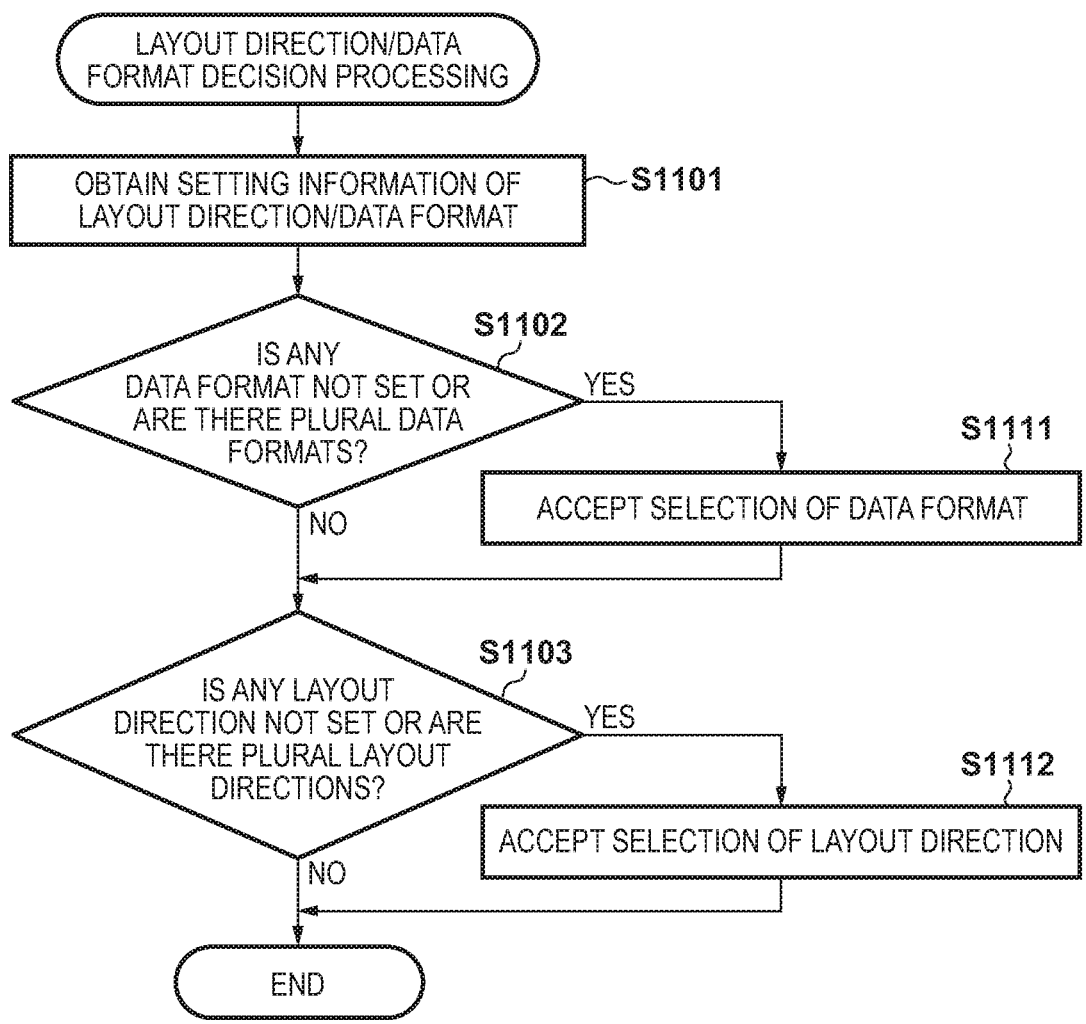
FIG. 11 is a flowchart for layout direction/data format decision processing in the medical information processing apparatus according to the first to third embodiments.

FIG. 11 is a flowchart for layout direction/data format decision processing in the medical information processing apparatus according to this embodiment. In step S1018 in FIG. 10B, the direction/format decision unit 404 executes layout direction/data format decision processing. The direction/format decision unit 404 can decide a layout direction and a data format based on the setting information 600-1 stored in advance. Upon starting the processing, the direction/format decision unit 404 obtains the setting information 600-1 (FIG. 6) (step S1101). If no data format is set or a plurality of data formats are set (YES in step S1102), the direction/format decision unit 404 accepts the selection of a data format (step S1111). When selecting a data format, the direction/format decision unit 404 displays, for example, a selection window (not shown) and accepts a selection input from the user.

In addition, if a layout direction has not been set or a plurality of layout directions have been selected (YES in step S1103), the direction/format decision unit 404 accepts the selection of the layout direction (step S1112). When selecting a layout direction, the direction/format decision unit 404 displays a selection window or the like (not shown) and accepts a selection input from the user as when selecting a data format.

(Paste Data Generation Processing Procedure)

Figure 12A:
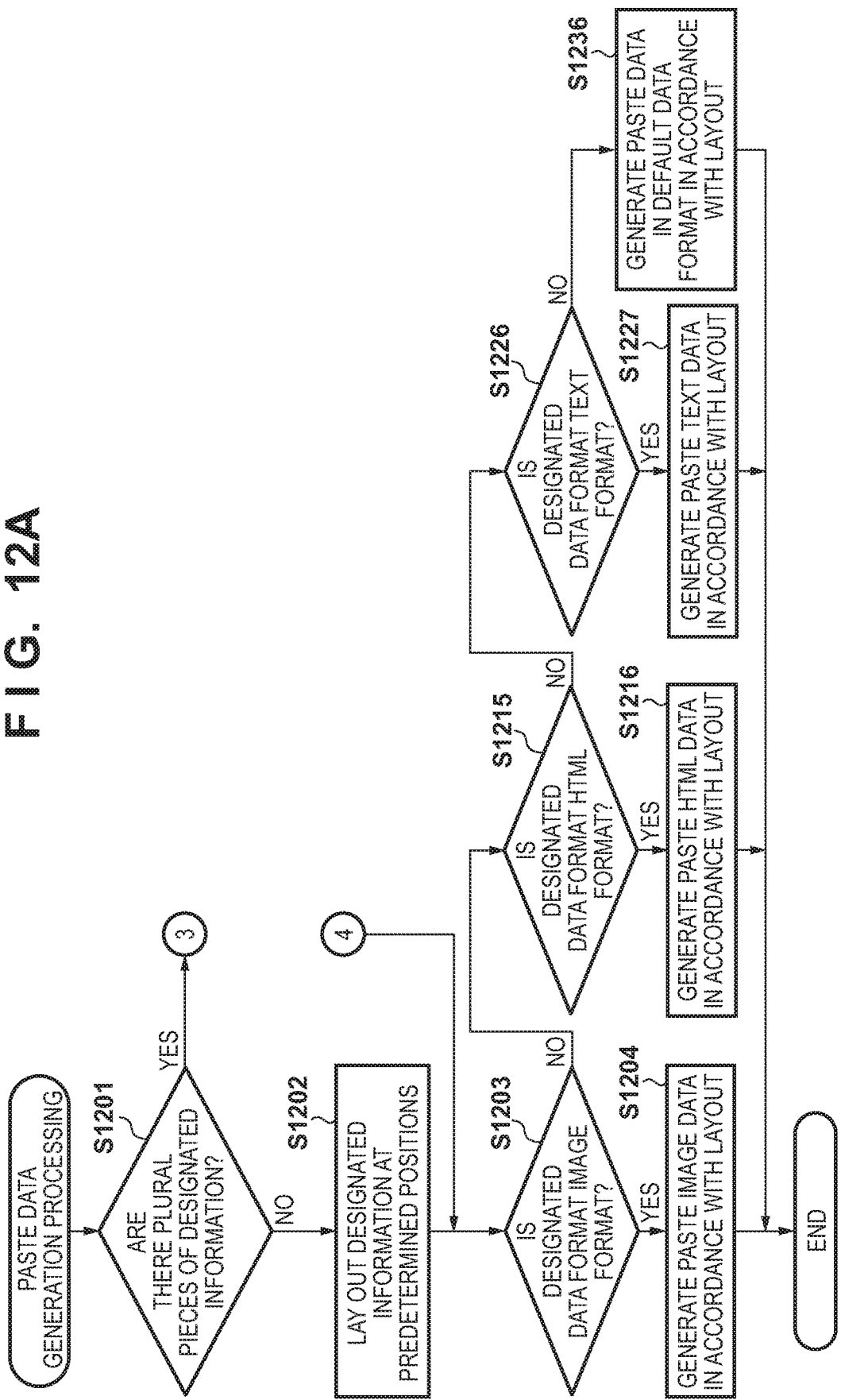

FIGS. 12A and 12B are flowcharts for paste data generation processing in the medical information processing apparatus according to this embodiment. In step S1019 in FIG. 10B, the paste data generating unit 405 executes paste data generation processing. Upon starting the processing, the paste data generating unit 405 checks whether there are a plurality of pieces of information designated as paste targets and stored in step S1017 in FIG. 10B (step S1201). If a plurality of pieces of information do not exist (NO in step S1201), the paste data generating unit 405 lays out the designated information at a predetermined position, for example, at an upper left position (step S1202). The process then advances to step S1203.

If a plurality of pieces of information exist (YES in step S1201), the paste data generating unit 405 checks whether the designated layout directions are vertical and horizontal (step S1211). If the layout directions are vertical and horizontal, the paste data generating unit 405 performs grouping of the information based on relation information, and lays out the information in each group in the horizontal direction while laying out the respective groups in the vertical direction, thereby generating paste data. If the designated layout directions are vertical and horizontal (YES in step S1211), the paste data generating unit 405 performs grouping of the designated information based on relation information (step S1212), and lays out the information in each group in the horizontal direction (step S1213). The paste data generating unit 405 further lays out the respective groups in the vertical direction (step S1214). The process then advances to step S1203.

In contrast, if the paste data generating unit 405 determines in step S1211 that the designated layout directions are vertical and horizontal, that is, the layout direction is the vertical or horizontal direction (NO in step S1211), the process advances to step S1221. In this case, a plurality of pieces of information obtained by classifying information about an imaging diagnosis include, for example, request information, image information, finding information, and diagnosis information, and the paste data generating unit 405 can perform grouping of the information based on the contents of the request information. When the contents of the request information indicate the purpose of closely examining the findings, the paste data generating unit 405 can perform, for each finding information, grouping of information related to the finding information based on relation information. Alternatively, if the contents of the request information indicate the purpose of diagnosis differentiation, the paste data generating unit 405 can perform, for each diagnosis information, grouping of information related to the diagnosis information based on relation information.

In specific processing, first of all, the paste data generating unit 405 checks whether a request purpose related to designated information is the purpose of closely examining findings (step S1221). If the request purpose related to the designated information is a purpose of closely examining findings (YES in step S1221), the paste data generating unit 405 performs grouping of information related to each finding information (step S1222), and the process advances to step S1223. If the request purpose related to designated information is not the purpose of closely examining findings (NO in step S1221), the paste data generating unit 405 checks whether the request purpose related to designated information is a purpose of diagnosis differentiation (step S1231).

If the request purpose related to designated information is the purpose of diagnosis differentiation (YES in step S1231), the paste data generating unit 405 performs, for each diagnosis information, grouping of related information (step S1232). The process then advances to step S1223. If the request purpose related to the designated information is not the purpose of diagnosis differentiation (NO in step S1231), the paste data generating unit 405 performs grouping of information related to each default information type (step S1241). The process then advances to step S1223. In this case, a default information type may be held as setting information for each user.

When the layout direction is either the vertical direction or the horizontal direction, the paste data generating unit 405 performs grouping of information based on relation information, and lays out the information in each group in the layout direction while laying out the respective groups in the layout direction, thereby generating paste data. When laying out information in the vertical or horizontal direction, the paste data generating unit 405 can change groups in accordance with the contents of the request information described above. In step S1223, the paste data generating unit 405 checks whether the designated layout direction is the vertical direction. If the designated layout direction is the vertical direction (YES in step S1223), the paste data generating unit 405 lays out the information in each group in the vertical direction (step S1224), and also lays out the respective groups in the vertical direction (step S1225). The process then advances to step S1203. If the designated layout direction is not the vertical direction (NO in step S1223), the paste data generating unit 405 checks whether the designated layout direction is the horizontal direction (step S1233). If the designated layout direction is the horizontal direction (YES in step S1233), the paste data generating unit 405 lays out the information in each group in the horizontal direction (step S1234), and also lays out the respective groups in the horizontal direction (step S1235). The process then advances to step S1203. If the designated layout direction is not the horizontal direction (NO in step S1233), the paste data generating unit 405 lays out the information in each group in the default direction (step S1242), and also lays out the respective groups in the default direction (step S1243). The process then advances to step S1203. In this case, the default layout direction may be held as setting information for each user.

In step S1203, the paste data generating unit 405 checks whether the designated data format is the image format. If the designated data format is the image format (YES in step S1203), the paste data generating unit 405 generates paste image data from the designated information in accordance with the layout (step S1204), and terminates the processing. If the designated data format is not the image format (NO in step S1203), the paste data generating unit 405 checks whether the designated data format is HTML (structured data) (step S1215). If the designated data format is HTML (YES in step S1215), the paste data generating unit 405 generates paste HTML data from the designated information in accordance with the layout (step S1216), and terminates the processing. In this case, layout based on HTML is performed by, for example, generating a table <table> storing pieces of information corresponding to "request", "image", "finding", "diagnosis", and the like, which are related to each other by "relation information", in the row or column direction of the display area. If the designated data format is not HTML (NO in step S1215), the paste data generating unit 405 checks whether the designated data format is the text format (step S1226). If the designated data format is the text format (YES in step S1226), the paste data generating unit 405 generates paste text data from the designated information in accordance with the layout (step S1227), and terminates the processing. If the designated data format is not the text format (NO in step S1226), the paste data generating unit 405 generates paste data in the default data format from the designated information in accordance with the layout (step S1236), and terminates the processing. In this case, the default data format may be held as setting information for each user.

According to this embodiment, when a structured interpretation report is pasted to a health record or the like, paste data are laid out in accordance with the contents of information and the structure of relation information. This operation makes it possible to perform a paste operation without impairing ease of understanding the contents of the report. For example, in laying out information in a line in the vertical or horizontal direction, changing each group when laying out information in accordance with a request purpose type can perform a paste operation without impairing ease of understanding the contents of the information.

Second Embodiment

The second embodiment will exemplify a medical information processing apparatus which obtains information concerning a paste destination, decides a layout direction and a data format based on the information concerning the paste destination, and pastes report information to health record information.

A system configuration, hardware arrangement, functional blocks, window arrangements, various types of information, layout direction, and layout examples concerning the medical information processing apparatus according to this embodiment are the same as those described in the first embodiment, and hence a description of them will be omitted. In addition, a paste data generation processing procedure is the same as that described in the first embodiment, and hence a description of the procedure will be omitted. Furthermore, the same reference numerals denote the same items as those described in other embodiments, and a description of them will be omitted.

(Main Processing Procedure According to Second Embodiment)

Figure 13A:
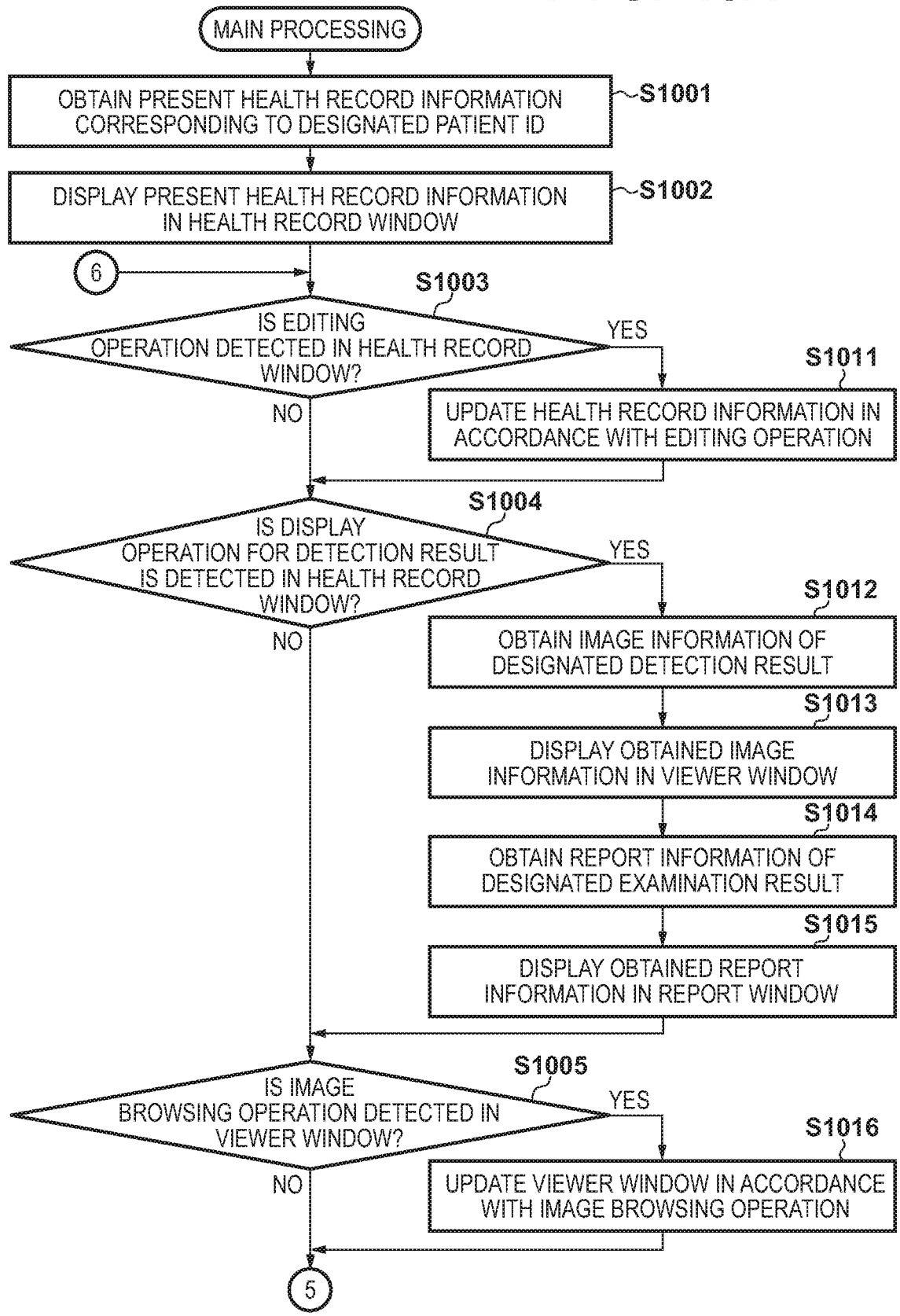
FIGS. 13A and 13B are flowcharts for main processing in the medical information processing apparatus according to the second embodiment.
Figure 13B:
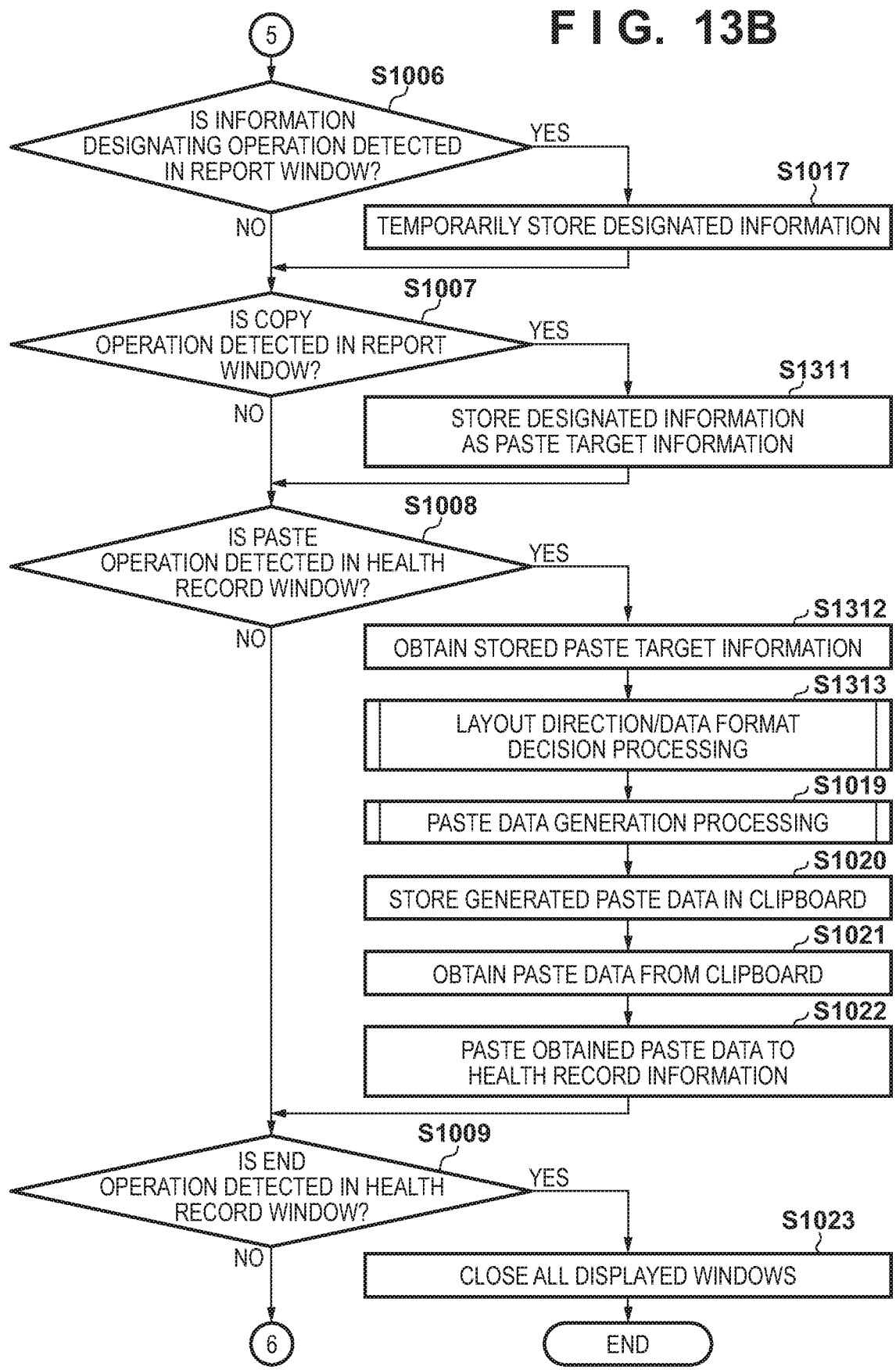

FIGS. 13A and 13B are flowcharts for main processing in the medical information processing apparatus according to this embodiment. In the main processing according to the embodiment, upon detecting a copy operation in a report window 330 (YES in step S1007), a paste instruction unit 403 stores designated information as paste target information (step S1311).

If the paste instruction unit 403 detects a paste operation in a health record window 310 (YES in step S1008), a direction/format decision unit 404 obtains the paste target information stored in step S1311 (step S1312). Subsequently, the direction/format decision unit 404 executes layout direction/data format decision processing in accordance with a paste destination, which will be described with reference to FIGS. 14A and 14B, (step S1313), and a paste data generating unit 405 generates paste data by executing paste data generation processing (step S1019).

(Layout Direction/Data Format Decision Processing Procedure According to Second Embodiment)

Figure 14A:
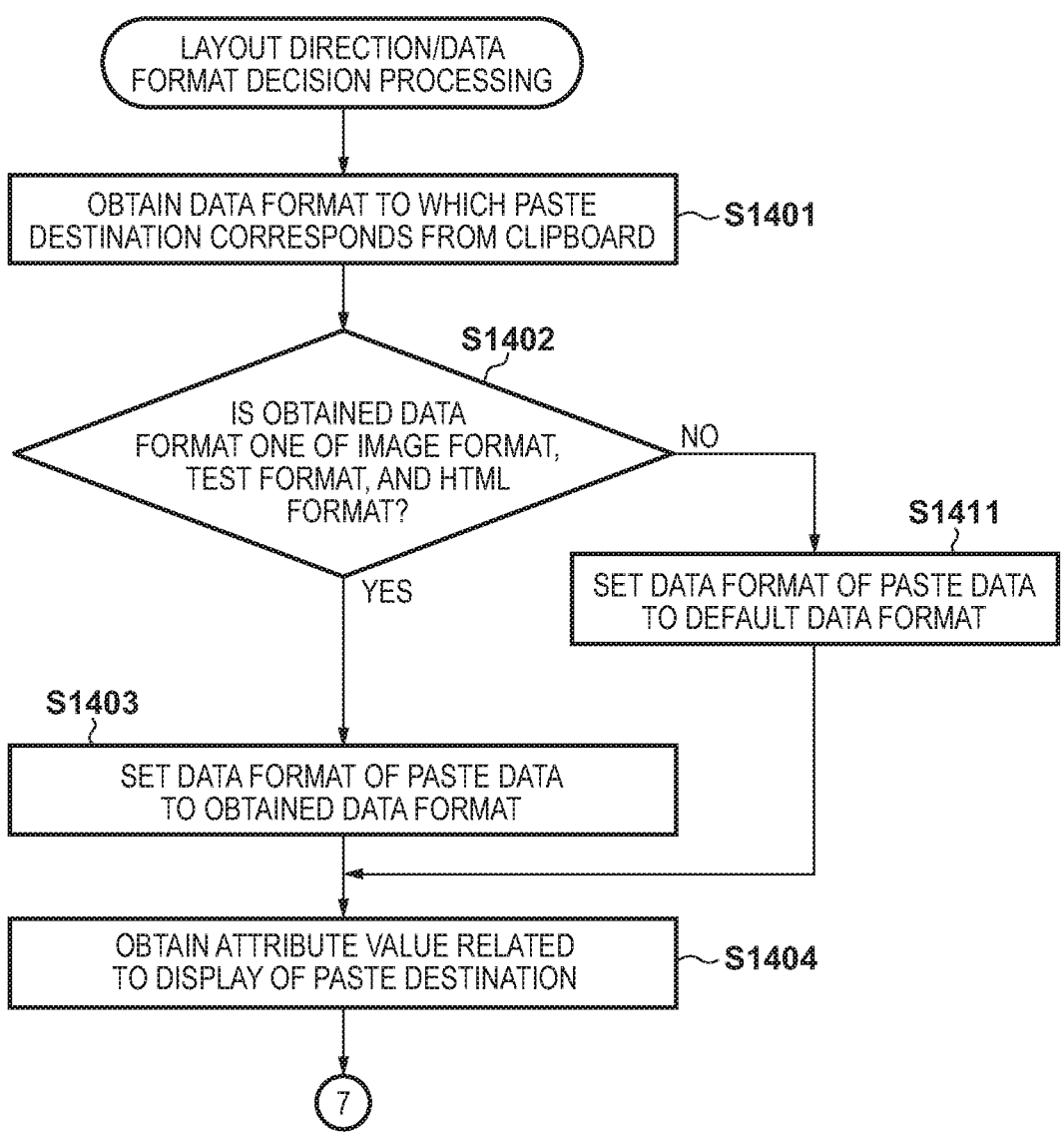
FIGS. 14A and 14B are flowcharts for layout direction/ data format decision processing in the medical information processing apparatus according to the second embodiment.
Figure 14B:
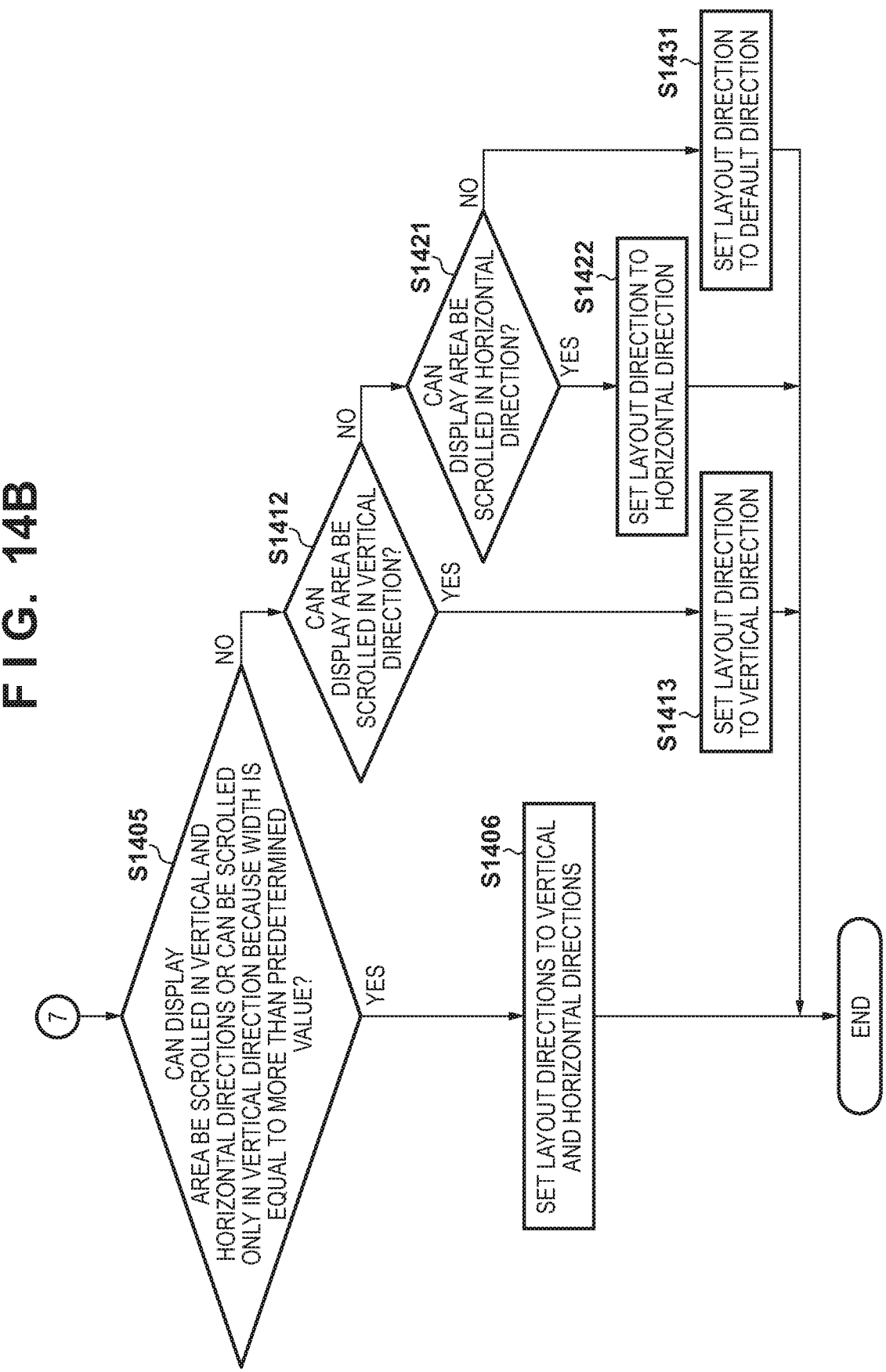

FIGS. 14A and 14B are flowcharts for layout direction/data format decision processing in the medical information processing apparatus according to this embodiment. The direction/format decision unit 404 executes layout direction/data format decision processing in step S1313 in FIG. 13B. The direction/format decision unit 404 can obtain a data format to which a paste destination corresponds, and decide the data format of paste information. Upon starting the processing, the direction/format decision unit 404 obtains a data format to which the paste destination corresponds from the clipboard (step S1401). In this case, the data format includes an image data format, text data format, and structured data format. If the obtained data format is either of the image data format, the text data format, and the structured data (HTML) format (YES in step S1402), the direction/format decision unit 404 sets the data format of paste target information (paste data) to the obtained data format (step S1403). The process then advances to step S1404. If the obtained data format is neither of the image data format, the text data format, and the structured data (HTML) format (NO in step S1402), the direction/format decision unit 404 sets the data format of the paste data to a default data format (step S1411). The process then advances to step S1404. In this case, the default data format may be held as setting information for each user. Although the data format to which the paste destination corresponds is obtained via the clipboard, the data format may be decided from information such as an object type.

The direction/format decision unit 404 can decide a layout direction based on an attribute value concerning the display of a paste destination. In step S1404, the direction/format decision unit 404 obtains an attribute value concerning the display of the paste destination (step S1404). This attribute value may be obtained by using a framework interface provided by the OS or by using a unique interface.

If a display area for a paste destination can be scrolled in both the vertical and horizontal directions or can be scrolled only in the vertical direction because the width is equal to or more than a predetermined value (YES in step S1405), the direction/format decision unit 404 sets the layout direction to the vertical and horizontal directions (step S1406), and terminates the processing.

If NO in step S1405, the direction/format decision unit 404 checks whether the area can be scrolled in the vertical direction (step S1412). If the area can be scrolled in the vertical direction (YES in step S1412), the direction/format decision unit 404 sets the layout direction to the vertical direction (step S1413), and terminates the processing. If the area cannot be scrolled in the vertical direction (NO in step S1412), the direction/format decision unit 404 checks whether the area can be scrolled in the horizontal direction (step S1421).

If the area can be scrolled in the horizontal direction (YES in step S1421), the direction/format decision unit 404 sets the layout direction to the horizontal direction (step S1422), and terminates the processing. If the area cannot be scrolled in the vertical direction (NO in step S1421), the direction/format decision unit 404 sets the layout direction to a default direction (step S1431), and terminates the processing. In this case, the default scroll direction may be held as setting information for each user.

Note that when the data format is HTML, the user may dynamically decide a layout direction and perform layout at the timing of displaying report information by using a button provided to switch between display and non-display of report information.

According to this embodiment, when pasting a structured interpretation report to a health record or the like, the user can perform a paste operation without impairing ease of understanding the contents of the report by laying out paste data in accordance with the contents of the information and the structure of relation information.

In addition, according to this embodiment, because a layout direction and a data format are decided in accordance with the display attributes of a paste destination, when there are a plurality of paste destination targets, it is possible to reduce the trouble of selecting a layout direction and a data format.

Third Embodiment

The third embodiment will exemplify a medical information processing apparatus which also adds information related to information designated as a paste target to the paste target.

Examples of a system configuration, hardware arrangement, functional blocks, window arrangement, various types of information, layout direction, and layout concerning the medical information processing apparatus according to this embodiment are the same as those described in the first embodiment, and hence a description of them will be omitted. In addition, a layout direction/data format decision processing procedure and a paste data generation processing procedure are the same as those described in the first embodiment, and hence a description of them will be omitted. Furthermore, the same reference numerals denote the same items as those described in other embodiments, and a description of them will be omitted.

(Setting Information According to Third Embodiment)

FIG. 15 shows an example of setting information in the medical information processing apparatus according to this embodiment. Setting information 600-2 according to the embodiment results from adding information related to information addition to the setting information (the data format and the layout direction) described in the first embodiment. The information related to information addition includes information indicating "selection" or "non-selection" concerning an examination information addition, report URL addition, image URL addition, and relation information addition. In this case, a report URL is a URL for browsing information as a paste target in the report window. Target information is highlighted in the report window. An image URL is a URL for displaying a representative image related to information as a paste target in the viewer window, and makes it possible to display, in the viewer window, an image on which a finding or diagnosis is based. In addition, relation information is information related to information as a paste target. When, for example, diagnosis information is designated, finding information or a representative image on which the diagnosis is based, recommended information corresponding to the diagnosis, and the like are set as paste targets altogether.

(Main Processing Procedure According to Third Embodiment)

Figure 16A:
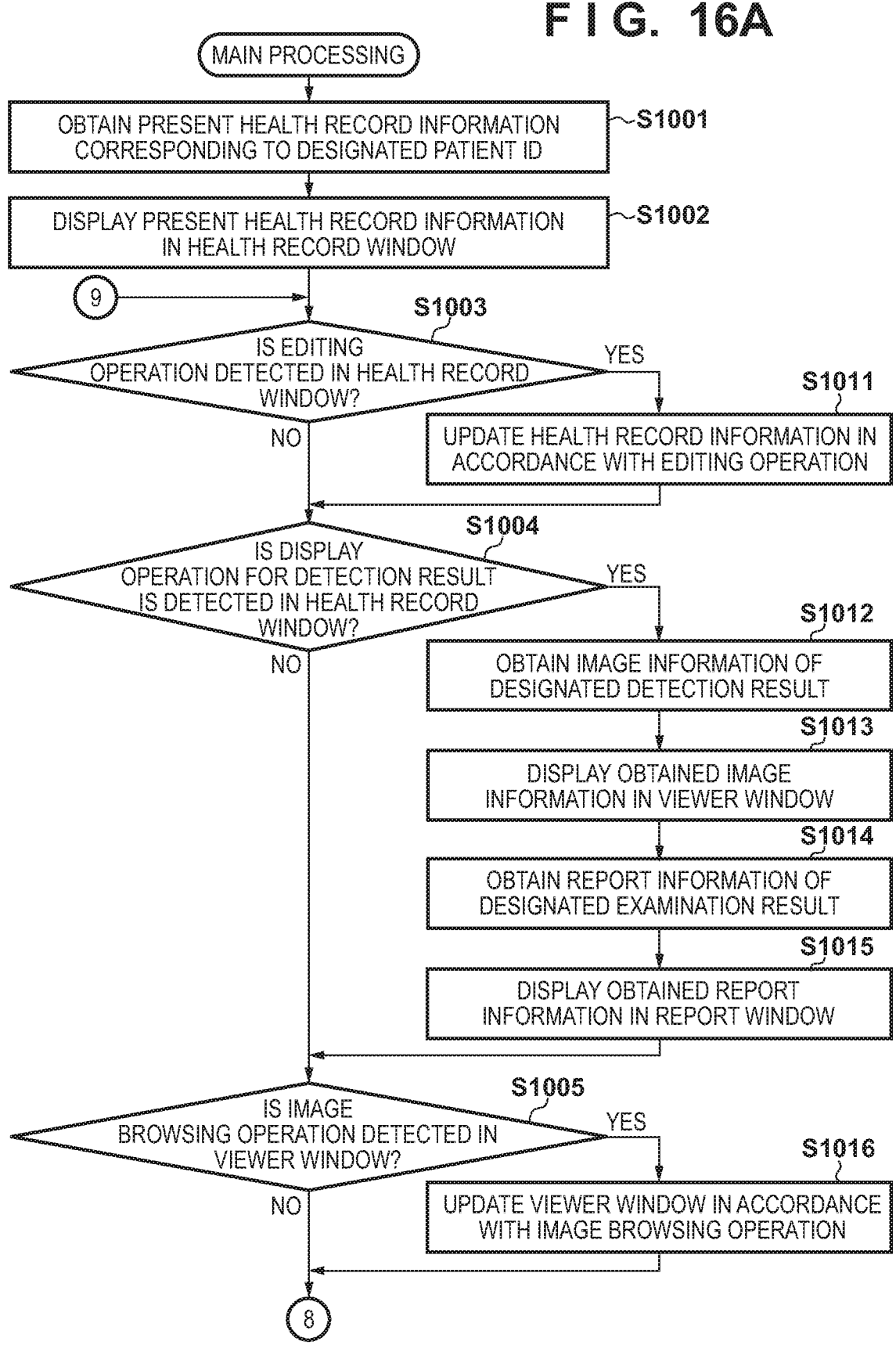
FIGS. 16A and 16B are flowcharts for main processing in the medical information processing apparatus according to the third embodiment.
Figure 16B:
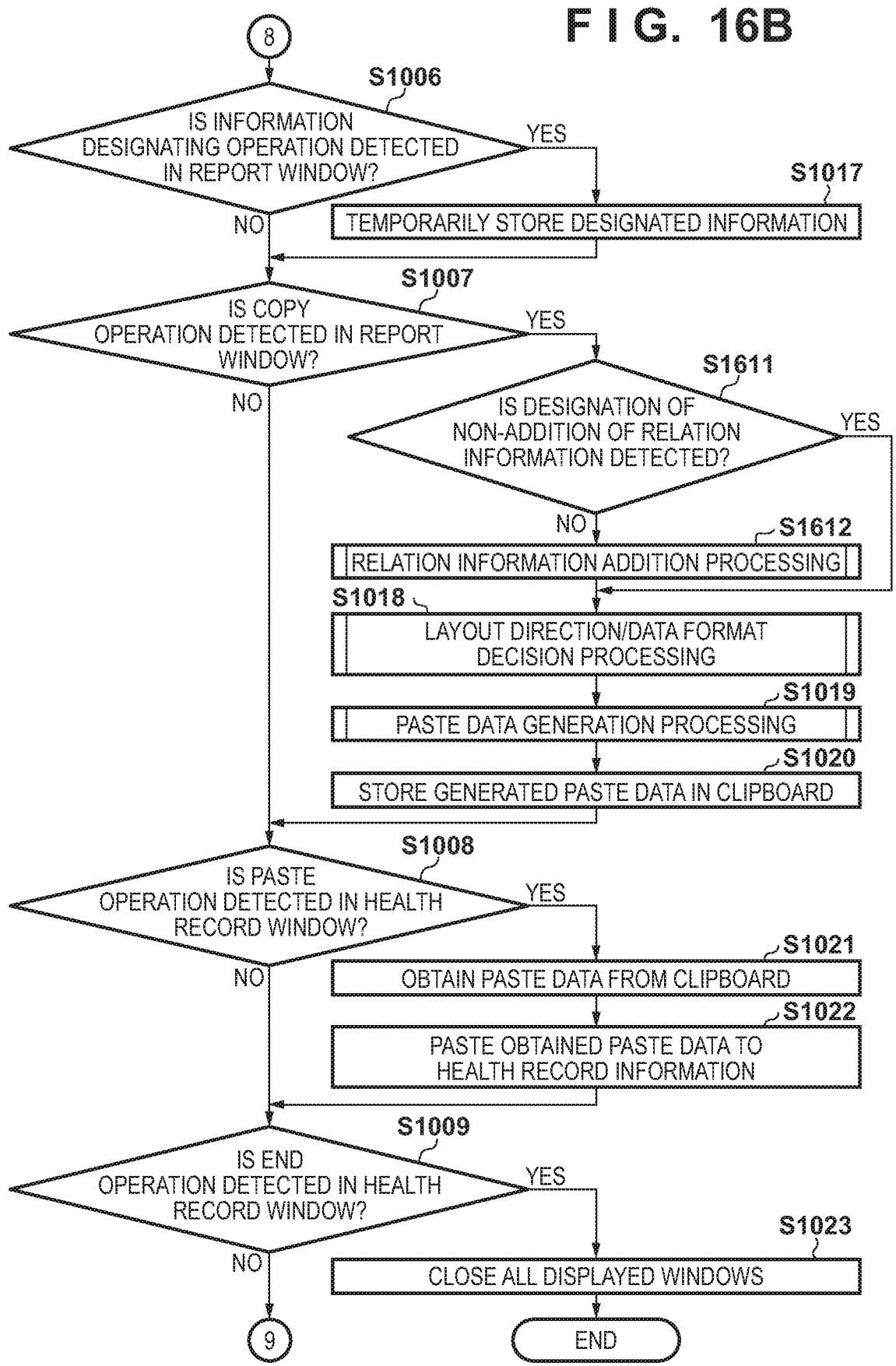

FIGS. 16A and 16B are flowcharts for main processing in the medical information processing apparatus according to this embodiment. In the main processing according to the embodiment, upon detecting a paste operation (copy operation) in a report window 330 (YES in step S1007), a paste instruction unit 403 checks whether the non-addition of relation information is designated at the time of issuing a paste instruction (step S1611).

If the non-addition of relation information is designated (YES in step S1611), the process advances to step S1018 to execute processing in and after step S1018. If the non-addition of relation information is not designated (NO in step S1611), that is, the addition of relation information is designated, the paste instruction unit 403 executes relation information addition processing to be described with reference to FIG. 17 (step S1612). The process then advances to step S1018. In this case, the designation of the non-addition of relation information is the operation of clarifying so as not to automatically add any relation information. For example, an operation such as pressing "Ctrl+Alt+C" is assigned to this operation. This designation may be held as setting information for each user.

(Relation Information Addition Processing Procedure According to Third Embodiment)

Figure 17:
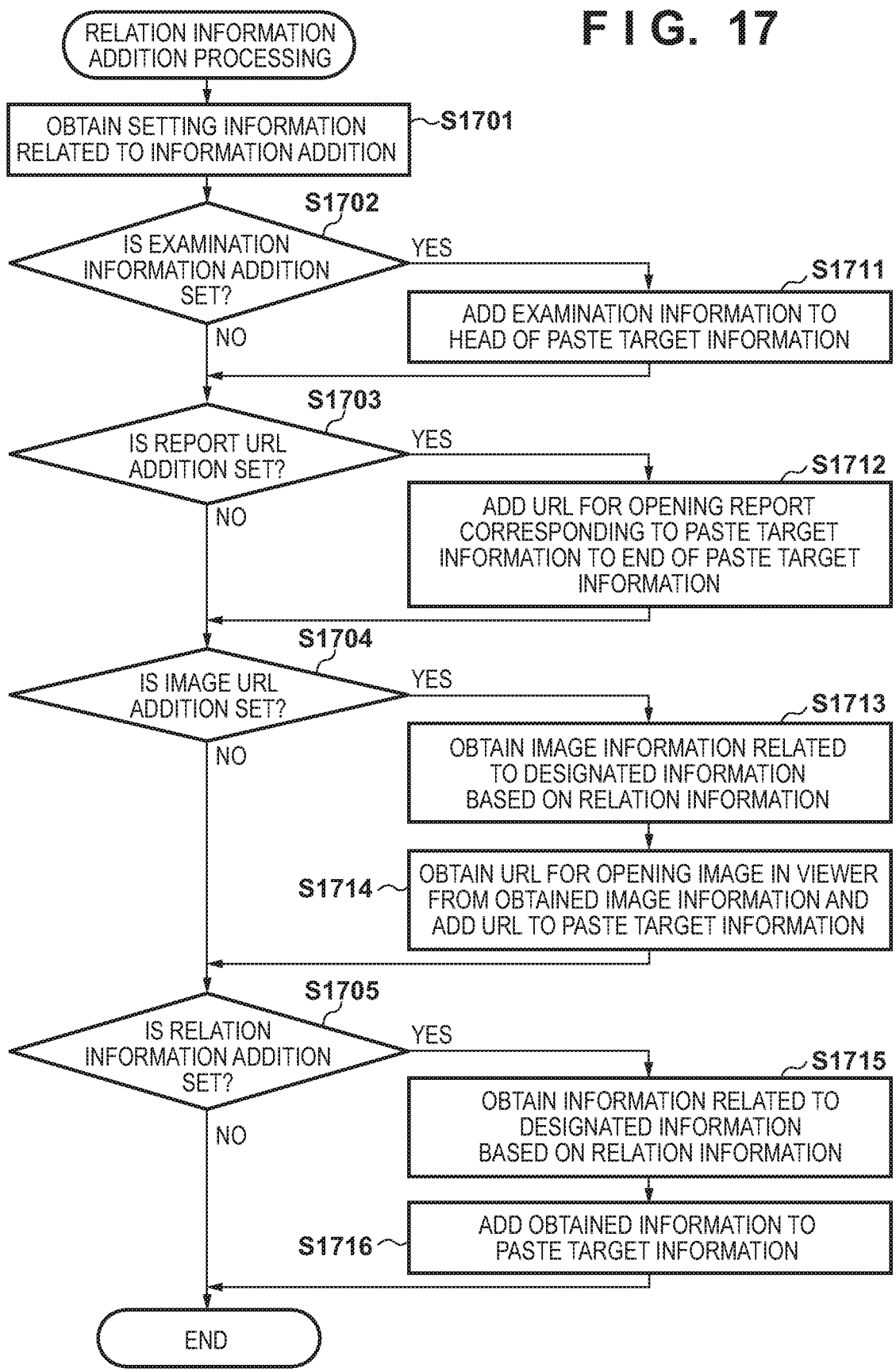
FIG. 17 is a flowchart for relation information addition processing in the medical information processing apparatus according to the third embodiment.

FIG. 17 is a flowchart for relation information addition processing in the medical information processing apparatus according to this embodiment. This relation information addition processing is executed in step S1612 in FIG. 16B. In the relation information addition processing, the paste instruction unit 403 obtains setting information related to information addition and adds information set as setting information to paste information (paste target information). The paste instruction unit 403 obtains information set as setting information and adds the information to paste information in accordance with relation information. Upon starting the processing, the paste instruction unit 403 obtains setting information related to information addition described with reference to FIG. 15 (step S1701).

If it is determined in step S1702 that examination information addition is not set (NO in step S1702), the process advances to step S1703. If examination information addition is set (YES in step S1702), the paste instruction unit 403 adds examination information to the head of paste target information (step S1711).

If it is determined in step S1703 that report URL addition is not set (NO in step S1703), the process advances to step S1704. If report URI addition is set (YES in step S1703), the paste instruction unit 403 adds a URL for displaying, on a report, information corresponding to the paste target information to the end of the paste target information (step S1712).

If it is determined in step S1704 that image URL addition is not set (NO in step S1704), the process advances to step S1705. In contrast to this, if image URL addition is set (YES in step S1704), the paste instruction unit 403 obtains the information of a representative image related to designated information based on relation information (step S1713). Subsequently, the paste instruction unit 403 obtains a URL for opening an image in the viewer from the obtained image information, and adds the URL to the paste target information (step S1714).

If it is determined in step S1705 that relation information addition is not set (NO in step S1705), the paste instruction unit 403 terminates this processing. If relation information addition is set (YES in step S1705), the paste instruction unit 403 obtains information related to the designated information based on the relation information (step S1715), and adds the obtained information to the past target information (step S1716). Upon adding the obtained information to the paste target information, the paste instruction unit 403 terminates this processing.

(Example of Health Record Window for Related Information Addition)

FIG. 18 shows an example of a health record window after report information pasting in the medical information processing apparatus according to this embodiment. Referring to FIG. 18, report information is pasted in a text format in a health record window 310-2, and added examination information 1801, added report URL 1802, and added image URL 1803 are additionally displayed in the health record window 310-2.

According to this embodiment, when pasting a structured interpretation report to a health record or the like, the user can perform a paste operation without impairing ease of understanding the contents of the report by laying out paste data in accordance with the contents of the information and the structure of relation information.

In addition, according to this embodiment, because only designating one piece of paste target information makes it possible to paste the information together with related information, it is possible to reduce the trouble of selecting a paste target.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-167287, filed Aug. 29, 2016, which is hereby incorporated by reference herein in its entirety.

What is claimed is:

1. A medical information processing apparatus which processes report information including a plurality of pieces of information obtained by classifying information about an imaging diagnosis and relation information indicating a relationship between the pieces of information, the apparatus comprising:
a memory storing a program;
and one or more processors which are configured to, by executing the program:
instruct pasting of the report information;
obtain display attributes concerning a scroll direction of a paste destination of the report information in accordance with an instruction, and to decide a layout direction of paste information based on the scroll direction of the paste destination; and
generate paste data obtained by laying out the paste information in accordance with the layout direction and the relation information,
wherein the layout direction is decided to be in a vertical direction when the paste destination can be scrolled in a vertical direction, and the layout direction is decided to be in a horizontal direction when the paste destination can be scrolled in a horizontal direction.

2. The apparatus according to claim 1, wherein the one or more processors are configured to
decide a data format of the paste information in addition to the layout direction, and
generate the paste data in accordance with the data format decided by the decision unit.

3. The apparatus according to claim 2, wherein a data format is decided based on setting information stored in advance.

4. The apparatus according to claim 3, wherein the data format includes an image data format, a text data format, and a structured data format.

5. The apparatus according to claim 2, wherein the one or more processors are configured to obtain a data format to which a paste destination corresponds and decide a data format of the paste information.

6. The apparatus according to claim 1, wherein the one or more processors are configured to
generate the paste data by performing grouping of the information based on the relation information, laying out information in each group in the layout direction, and laying out the groups in the layout direction.

7. The apparatus according to claim 1, wherein the plurality of pieces of information include request information, image information, finding information, and diagnosis information.

8. The apparatus according to claim 7, wherein the one or more processors are configured to perform grouping of the information based on contents of the request information.

9. The apparatus according to claim 8, wherein the one or more processors are configured to, when the contents of the request information indicate a purpose of closely examining findings, perform, for each finding information, grouping of information related to the finding information based on the relation information, and when the contents of the request information indicate a purpose of diagnosis differentiation, perform, for each diagnosis information, grouping of information related to the diagnosis information based on the relation information.

10. The apparatus according to claim 8, wherein the one or more processors are configured to, when laying out the information in the vertical direction or the horizontal direction, change a group in accordance with the contents of the request information.

11. The apparatus according to claim 1, wherein the one or more processors are configured to, when the layout directions are vertical and horizontal directions, generate the paste data by performing grouping of the information based on the relation information, laying out information in each group in the horizontal direction, and laying out the groups in the vertical direction.

12. The apparatus according to claim 1, wherein the a layout direction is decided based on an attribute value concerning display of a paste destination.

13. The apparatus according to claim 1, wherein the one or more processors are configured to obtain setting information concerning information addition, and add information set in the setting information to the paste information.

14. The apparatus according to claim 13, wherein the one or more processors are configured to obtain information set in the setting information and add the information to the paste information in accordance with the relation information.

15. The apparatus according to claim 1, the one or more processors being configured to designate information constituting the report information as information as a target subjected to the pasting operation;
instruct all or part of the report information based on designation made by the designation unit; and
decide a layout direction of the paste information in accordance with an instruction from the instruction unit.

16. A medical information processing system including a medical information processing apparatus which processes report information including a plurality of pieces of information obtained by classifying information about an imaging diagnosis and relation information indicating a relationship between the pieces of information, the medical information processing apparatus comprising:
a memory storing a program; and
one or more processors configured to, by executing the program:
instruct pasting of the report information;
obtain display attributes concerning a scroll direction of a paste destination of the report information in accordance with an instruction, and to decide a layout direction of paste information based on the scroll direction of the paste destination; and
generate paste data obtained by laying out the paste information in accordance with the layout direction,
wherein the layout direction is decided to be in a vertical direction when the paste destination can be scrolled in a vertical direction, and the layout direction is decided to be in a horizontal direction, when the paste destination can be scrolled in a horizontal direction.

17. A medical information processing method of processing report information including a plurality of pieces of information obtained by classifying information about an imaging diagnosis and relation information indicating a relationship between the pieces of information, the method comprising:
- instructing pasting of the report information;
- obtaining display attributes concerning a scroll direction of a paste destination of the report information in accordance with an instruction in the instructing, and deciding a layout direction of paste information based on the scroll direction of the paste destination;
- generating paste data obtained by laying out the paste information in accordance with the layout direction and the relation information;
- deciding the layout direction in a vertical direction when the paste destination can be scrolled in a vertical direction; and
- deciding the layout direction in a horizontal direction when the paste destination can be scrolled in a horizontal direction.

18. A non-transitory computer-readable storage medium storing a program for causing a computer to execute steps in a medical information processing method of processing report information including a plurality of pieces of information obtained by classifying information about an imaging diagnosis and relation information indicating a relationship between the pieces of information, the method comprising:
- instructing pasting of the report information;
- obtaining display attributes concerning a scroll direction of a paste destination of the report information in accordance with an instruction in the instructing, and deciding a layout direction of paste information based on the scroll direction of the paste destination;
- generating paste data obtained by laying out the paste information in accordance with the layout direction and the relation information;
- deciding the layout direction in a vertical direction when the paste destination can be scrolled in a vertical direction; and
- deciding the layout direction in a horizontal direction when the paste destination can be scrolled in a horizontal direction.

19. A medical information processing apparatus which processes report information including a plurality of pieces of information obtained by classifying information about an imaging diagnosis and relation information indicating a relationship between the pieces of information, the apparatus comprising:
- a memory storing a program; and
- one or more processors configured to, by executing the program:
  - instruct pasting of the report information;
  - obtain display attributes concerning a scroll direction of a paste destination of the report information in accordance with an instruction, and to decide an arrangement of contents of paste information based on the scroll direction of the paste destination; and
  - generate paste data obtained by laying out the contents of paste information in accordance with the arrangement and the relation information,
  - wherein the arrangement of contents is decided to be in a vertical direction when the paste destination can be scrolled in a vertical direction, and the arrangement of contents is decided to be in a horizontal direction, when the paste destination can be scrolled in a horizontal direction.

20. A medical information processing method of processing report information including a plurality of pieces of information obtained by classifying information about an imaging diagnosis and relation information indicating a relationship between the pieces of information, the method comprising:
- instructing pasting of the report information;
  - obtaining display attributes concerning a scroll direction of a paste destination of the report information in accordance with an instruction from the instruction unit, and deciding an arrangement of contents of paste information based on the scroll direction of the paste destination;
  - generating paste data obtained by laying out the contents of paste information in accordance with the arrangement and the relation information;
  - deciding the arrangement of contents in a vertical direction when the paste destination can be scrolled in a vertical direction; and
  - deciding the arrangement of contents in a horizontal direction when the paste destination can be scrolled in a horizontal direction.

21. A non-transitory computer-readable storage medium storing a program for causing a computer to execute steps in a medical information processing method of processing report information including a plurality of pieces of information obtained by classifying information about an imaging diagnosis and relation information indicating a relationship between the pieces of information, the method comprising:
- instructing pasting of the report information;
  - obtaining display attributes concerning a scroll direction of a paste destination of the report information in accordance with an instruction from the instruction unit, and deciding an arrangement of contents of paste information based on the scroll direction of the paste destination;
- generating paste data obtained by laying out the contents of paste information in accordance with the arrangement and the relation information;
- deciding the arrangement of contents in a vertical direction when the paste destination can be scrolled in a vertical direction; and
- deciding the arrangement of contents in a horizontal direction, when the paste destination can be scrolled in a horizontal direction.

22. An information processing apparatus which processes report information including a plurality of pieces of information and relation information indicating a relationship between the pieces of information, the apparatus comprising:
- a memory storing a program;
- and one or more processors configured to, by executing the program:
- instruct pasting of the report information;
- obtain display attributes concerning a scroll direction of a paste destination of the report information in accordance with an instruction, and to decide a layout direction of paste information based on the scroll direction of the paste destination; and
- generate paste data obtained by laying out the paste information in accordance with the layout direction and the relation information, wherein the layout direction is decided to be in a vertical direction when the paste destination can be scrolled in a vertical direction, and the layout direction is decided to be in a horizontal direction when the paste destination can be scrolled in a horizontal direction.

23. The information apparatus according to claim 22, wherein the paste data is generated by performing grouping of the information based on the relation information, laying out information in each group in the layout direction, and laying out the groups in the layout direction.

24. The information apparatus according to claim 22, wherein the setting information concerning information addition is obtained, and information set in the setting information is added to the paste information.

25. The information apparatus according to claim 24, wherein the information set in the setting information is obtained and the information is added to the paste information in accordance with the relation information.

* * * * *